US008163461B2

(12) United States Patent
Ober et al.

(10) Patent No.: US 8,163,461 B2
(45) Date of Patent: Apr. 24, 2012

(54) PHOTOACID GENERATOR COMPOUNDS AND COMPOSITIONS

(75) Inventors: Christopher K. Ober, Ithaca, NY (US); Yi Yi, Urbana, IL (US)

(73) Assignee: Cornell Research Foundation, Inc., Ithaca, NY (US)

( * ) Notice: Subject to any disclaimer, the term of this patent is extended or adjusted under 35 U.S.C. 154(b) by 477 days.

(21) Appl. No.: 12/421,544

(22) Filed: Apr. 9, 2009

(65) Prior Publication Data

US 2009/0258315 A1 Oct. 15, 2009

Related U.S. Application Data

(60) Provisional application No. 61/043,602, filed on Apr. 9, 2008.

(51) Int. Cl.
 G03F 7/004 (2006.01)
 G03F 7/30 (2006.01)
 C07H 15/04 (2006.01)
 C07D 309/10 (2006.01)

(52) U.S. Cl. ............ 430/270.1; 430/326; 430/330; 430/907; 430/921; 536/1.11; 536/4.1; 536/17.4; 549/415; 562/113

(58) Field of Classification Search ......... 430/270.1, 430/326, 330; 536/1.11, 4.1, 17.4; 549/415; 662/113
See application file for complete search history.

(56) References Cited

U.S. PATENT DOCUMENTS

| | | | |
|---|---|---|---|
| 5,468,902 | A | 11/1995 | Castellanos et al. |
| 5,514,728 | A | 5/1996 | Lamanna et al. |
| 5,554,664 | A | 9/1996 | Lamanna et al. |
| 5,565,500 | A | 10/1996 | Meier et al. |
| 5,710,320 | A | 1/1998 | Vogel et al. |
| 5,981,140 | A | 11/1999 | Sato et al. |
| 6,200,728 | B1 | 3/2001 | Cameron et al. |
| 6,485,883 | B2 | 11/2002 | Kodama et al. |
| 6,692,893 | B2 | 2/2004 | Ohsawa et al. |
| 6,749,987 | B2 | 6/2004 | Kodama et al. |
| 6,908,722 | B2 | 6/2005 | Ebata et al. |
| 6,924,323 | B2 | 8/2005 | Ishihara et al. |
| 6,929,896 | B2 | 8/2005 | Yamato et al. |
| 6,949,329 | B2 | 9/2005 | Endo et al. |
| 7,105,267 | B2 | 9/2006 | Hatakeyama et al. |
| 7,122,291 | B2 | 10/2006 | Padmanaban et al. |
| 7,163,776 | B2 | 1/2007 | Sasaki et al. |
| 7,288,359 | B2 | 10/2007 | Iwasawa et al. |
| 7,393,627 | B2 | 7/2008 | Ober et al. |
| 7,618,765 | B2 | 11/2009 | Nishi et al. |
| 7,622,240 | B2 * | 11/2009 | Sooriyakumaran et al. ............ 430/270.1 |
| 7,824,839 | B2 | 11/2010 | Ober et al. |
| 2002/0102491 | A1 | 8/2002 | Kodama et al. |
| 2002/0197558 | A1 | 12/2002 | Ferreira et al. |
| 2003/0027061 | A1 | 2/2003 | Cameron et al. |
| 2003/0113658 | A1 | 6/2003 | Ebata et al. |
| 2003/0170561 | A1 | 9/2003 | Iwasawa et al. |
| 2003/0180596 | A1 | 9/2003 | Yoshimura et al. |
| 2003/0219679 | A1 | 11/2003 | Sasaki et al. |
| 2004/0033440 | A1 | 2/2004 | Maeda et al. |
| 2004/0087690 | A1 | 5/2004 | Lamanna et al. |
| 2005/0158655 | A1 | 7/2005 | Lamanna et al. |
| 2005/0208420 | A1 | 9/2005 | Ober et al. |
| 2006/0194144 | A1 * | 8/2006 | Sooriyakumaran et al. ............ 430/270.1 |
| 2007/0148592 | A1 | 6/2007 | Wada et al. |
| 2008/0227032 | A1 | 9/2008 | Ober et al. |
| 2009/1004212 | | 2/2009 | Kamimura et al. |
| 2009/0075202 | A1 | 3/2009 | Kodama et al. |
| 2009/0136868 | A1 | 5/2009 | Ober et al. |
| 2011/0008732 | A1 | 1/2011 | Ober et al. |

FOREIGN PATENT DOCUMENTS

| | | |
|---|---|---|
| CN | 1066446 | 11/1992 |
| DE | 295421 | 10/1991 |
| EP | 1270553 A2 | 1/2003 |
| JP | 2001-159812 | 6/2001 |
| WO | WO-02/18332 A1 | 3/2002 |
| WO | WO-2007/124092 A2 | 11/2007 |

OTHER PUBLICATIONS

"U.S. Appl. No. 11/080,658, Non-Final Office Action mailed Jul. 24, 2007", 13 pgs.
"U.S. Appl. No. 11/080,658, Response filed Nov. 26, 2007 to Non-Final Office Action mailed Jul. 24, 2007", 8 pgs.
"U.S. Appl. No. 11/080,658, Non-Final Office Action mailed Dec. 28, 2006", 6 pgs.
"U.S. Appl. No. 11/080,658, Notice of Allowance mailed Feb. 26, 2008", 6 pgs.
"U.S. Appl. No. 11/080,658, Response filed Apr. 30, 2007 to Non-Final Office Action mailed Dec. 28, 2006", 18 pgs.
"U.S. Appl. No. 12/129,507, Non-Final Office Action mailed Dec. 12, 2008", 10 pgs.
"International Application Serial No. PCT/U805/08678, International Search Report mailed Mar. 3, 2006", 2 pgs.
"International Application Serial No. PCT/U805/08678, Written Opinion mailed Mar. 3, 2006", 4 pgs.
"International Application Serial No. PCT/US07/09714, International Search Report mailed Oct. 15, 2007", 3 pgs.
"International Application Serial No. PCT/US07/09714, Written Opinion mailed Oct. 15, 2007", 6 pgs.
Blotny, G., "A New, Mild Preparation of Sulfonyl Chlorides", *Tetrahedron Letters*, 44, (2003), 1499-1501.
Crivello, J. V., et al., "Diaryliodonium Salts. A New Class of Photoinitiators for Cationic Polymerization", *Macromolecules*, 10(6), (Nov.-Dec. 1977), 1307-1315.

(Continued)

*Primary Examiner* — John Chu
(74) *Attorney, Agent, or Firm* — Schwegman, Lundberg & Woessner P.A.

(57) ABSTRACT

The invention provides various photoacid generator compounds and ionic components thereof. Photoresist compositions that include the ions and non-ionic photoacid generator compounds are also provided. The invention further provides methods of making and using the photoacid generator compounds and photoresist compositions disclosed herein. The compounds and compositions are useful as photoactive components in chemically amplified resist compositions for use in, for example, various microfabrication applications.

28 Claims, No Drawings

OTHER PUBLICATIONS

Crivello, J. V., et al., "Synthesis and Characterization of Second-Generation Dialkylphenacylsulfonium Salt Photoinitiators", *Macromolecules*, 33(3), (2000), 825-832.

De Vleeschauwer, M., et al., "Remarkably Mild and Simple Preparations of Sulfinates, Sulfonyl Chlorides and Sulfonamides From Thioanisoles", *Synlett*, (Apr. 1997), 375-377.

Ding, Y., et al., "$LnCl_3$(cat.)/En Promoted Hydroperfluoroalkylation of a β—Unsaturated Esters With Perfluoroalkyl Iodides", *Tetrahedron Letters*, 33(52), (1992), 8119-8120.

Feiring, A. E., et al., "Aromatic Monomers With Pendant Fluoroalkylsulfonate and Sulfonimide Groups", *Journal of Fluorine Chemistry*, 105, (2000), 129-135.

Feiring, A. E., "Reaction of Perfluoroalkylk Iodides With Electron Donor Nucleophiles. Addition of Perfluoroalkyl Iodides to Olefins Initiated by Electron Transfer", *Journal of Organic Chemistry*, 50(18), (1985), 3269-3274.

Gisler, M., et al., "Neue Methods zur Phasentransfer-Katalysierfen Sulfodechlorierung von 1-Chlor-2,4-dinitrobenzol [New Method for the Phase Transfer-Catalyzed Sulfodechlorination of 1-chloro-2,4-dinitrobenzene]", *Anciewandte Chemie*, 93(2), (Abstract Only), (1981), 1 pg.

Gisler, M., et al., "Novel Method for the Phase-Transfer Catalyzed Sulfodechlorination of 1-Chloro-2,4-dinitrobenzene", *Angew. Chem. Int. Ed. Engl.*, 20(2), (1981), 203-204.

Guo, X.-C., et al., "The First Example of Addition Reactions of Sterically Hindered Terminal Olefins, α-Substituted Styrenes, With Perfluoroalkyl Iodides Initiated by Sodium Dithionite", *Journal of Fluorine Chemistry*, 93, 1999 , 81-86.

Hasan, A., et al., "Photolabile Protecting Groups for Nucleosides: Synthesis and Photodeprotection Rates", *Tetrahedron*, 53(12), (1997), 4247-4267.

Houlihan, F. M., et al., "Design, Synthesis, Characterization, and Use of All-Organic Nonionic Photogenerators of Acid", *Chemistry of Materials*, 3(3), (1991), 462-471.

Hu, C.-M., et al., "Cobaloxime-Catalyzed Hydroperfluoroalkylation of Electron-Deficient Alkenes With Perfluoroalkyl Halides: Reaction and Mechanism", *Journal of Organic Chemistry*, 57(12), (1992), 3339-3342.

Hu, C.-M., et al., "Reaction of Perfluoroalkanesulfinates With Allyl and Propargy Halides. A Convenient Synthesis of 3-(Perfluoroalky)prop-1-enes and 3-(Perfluoroalkyl)allenes", *Journal of Organic Chemistry*, 56(8), (1991), 2801-2804.

Hu, C.-M., et al., "Redox-Initiated Per(poly)fluoroalkylation of Olefins by Per(poly)fluoroalkyl Chlorides", *Journal of Organic Chemistry*, 56(22), (1991), 6348-6351.

Imazeki, S., et al., "Facile Method for the Preparation of Triarylsulfonium Bromides Using Grignard Reagents and Chlorotrimethylsilane as an Activator", *Synthesis*,10, (2004), 1648-1654.

Iwashima, C., et al., "Synthesis of i- and g-Line Sensitive Photoacid Generators and Their Application to Photopolymer Systems", *Journal of Photopolymer Science and Technology*, 16(1), (2003), 91-96.

Long, Z.-Y., et al., "The Activation of Carbon-Chlorine Bonds in Per- and Polyfluoroalkyl Chlorides: DMSO-Induced Hydroperfluoroalkylation of Alkenes and Alkynes with Sodium Dithionite", *Journal of Organic Chemistry*, 64(13), 1999 , 4775-4782.

Lu, X., et al., "Samarium Diiodide Initiated Addition Reaction of Fluoroalkyl Iodides to Olefins", *Tetradedron Letters*, 29(40), (1988), 5129-5130.

Okamura, H., et al., "Evaluation of Quantum Yields for Decomposition of I-Line Sensitive Photoacid Generators", *Journal of Photopolymer Science and Technology*, 16(5), (2003), 701-706.

Okamura, H., et al., "I-Line Sensitive Photoacid Generators and Their Use for Photocrosslinking of Polysilane/diepoxyfluorene Blend", *Journal of Photopolymer Science and Technology*, 16(1), (2003), 87-90.

Richard, J. P., et al., "The Effect of β-Fluorine Substituents on the Rate and Equilibrium Constants for the Reactions of α-Substituted 4-Methoxybenzyl Carbocations and on the Reactivity of a Simple Quinone Methide", *Journal of American Chemical Society*, 112(26), (1990), 9513-9519.

Serafinowski, P. J., et al., "Novel Photoacid Generators for Photodirected Oligonucleotide Synthesis", *Journal of the American Chemical Society*, 125, (2003), 962-965.

Shirai, M., et al., "Development of Novel Photosensitive Polymer Systems Using Photoacid and Photobase Generators", *Journal of Photopolymer Science and Technology*,15(5), (2002), 715-730.

Shirai, M., et al., "Photoacid and Photobase Generators: Chemistry and Applications to Polymeric Materials", *Progress in Polymer Science*, 21(1), (1996), 1-45.

Willenbring, R. J., et al., "New Pentafluorothio($SF_5$) Alkylsulfonic Acids", *Canadian Journal of Chemistry*, 67, (1989), 2037-2040.

Zhao, Z., "Synthesis of Sodium Picrylsulfonate", *Huaxue Shiji*, 8(5), (Abstract Only), (1986), 320 (1 pg.).

Zou, X., et al., "Synthesis of Polyfluoroalkyl-γ-lactones From Polyfluoroalkyl Halides and 4-pentenoic Acids", *Tetrahedron*, 59, (2003), 2555-2560.

"U.S. Appl. No. 12/255,266, Response filed May 17, 2010 to Restriction Requirement Apr. 30, 2010", 6 pgs.

"U.S. Appl. No. 12/255,266, Notice of Allowance mailed Jul. 2, 2010", 6 pgs.

"U.S. Appl. No. 12/255,266, Restriction Requirement mailed Apr. 30, 2010", 6 pgs.

\* cited by examiner

PHOTOACID GENERATOR COMPOUNDS AND COMPOSITIONS

CROSS REFERENCES TO RELATED APPLICATIONS

This application claims priority under 35 U.S.C. §119(e) to U.S. Provisional Patent Application No. 61/043,602, filed Apr. 9, 2008, which is incorporated herein by reference.

BACKGROUND

In the semiconductor industry, chemically amplified resist (CAR) technology is essential for the fabrication of micro- and nano-size patterns. Photoacid generators (PAGs) are a key component in a CAR system, particularly for deep UV (DUV) lithography, including 248 nm and 193 nm lithography, and for next generation lithography (NGL), such as electron-beam and extreme-UV (EUV) lithography. PAGs are primarily used for lithography in the semiconductor industry but are also useful for reactive coating applications.

Several acid-catalyzed chemically amplified resist compositions are well known in the art. Chemically amplified resist compositions generally include a PAG and an acid sensitive polymer (resist). Upon exposure to radiation (e.g., x-ray radiation, ultraviolet radiation), the photoacid generator, by producing a proton, creates a photo-generated catalyst (usually a strong acid) during the exposure to radiation. The acid may act as a catalyst for further reactions during a post-exposure bake (PEB). For example, the acid generated may facilitate deprotection or cross-linking in the photoresist. Generation of acid from the PAG does not necessarily require heat. However, many known chemically amplified resists require a post-exposure bake (PEB) to complete the reaction between the acid moiety and the acid labile component. Chemical amplification type resist materials include positive working materials that leave unexposed material with the exposed areas removed and negative working materials that leave exposed areas with the unexposed areas removed.

Photoacid generators (PAGs) play a critical role in chemically amplified resist systems. Among the various classes of ionic and nonionic PAGs that have been developed, one of the most widely used classes is the perfluorinated onium salts. Government regulation has rendered many of the most effective PAGs no longer commercially viable, including those based on perfluorooctyl sulfonates (PFOS). In addition to environmental concerns, the PFOS-based PAGs are a concern because of their fluorous self-assembly and their diffusion characteristics at smaller dimensions.

Previous efforts to develop new PAGs have focused mainly on improving the photosensitive onium cation to increase the quantum yield or to improve absorbance. The nature of the photoacid produced upon irradiation of the PAG is directly related to the anion of the ionic PAG. Difference in acid strength, boiling point, size, miscibility, and stability of the photoacid produced can affect parameters related to photoresist performance, such as deprotection (or cross-linking) efficiency, photospeed, post-exposure bake (PEB) sensitivity, post-exposure delay (PED) stability, resolution, standing waves, image profiles, and acid volatility. Because PFOS-based PAGs are being phased out and current commercial PAGs have significant drawbacks with respect to the previously mentioned properties, new PAGs are needed that can help resolve these environmental and performance issues.

SUMMARY

The invention provides new photoacid generators, including non-ionic PAGs and anionic components of PAGs. These novel PAGs and PAG components include a carbohydrate or saccharide moiety. Such PAGs can be referred to as "sweet PAGs". The invention provides improved homogeneous distribution in a resist and appropriate mobility of the photogenerated acid can be obtained. While maintaining PAG performance characteristics, the sweet PAGs are free of perfluorinated precursors and therefore environmentally compatible. At the same time, the new PAGs favorably address environmental issues, including the need to reduce or eliminate the use of PFOSs.

To address environmental concerns related to the use of PFOS PAGs, sulfonic acids have been developed that contain fewer fluorinated carbons than typically found in PFOS. Perfluoro segments have been replaced with various functional groups that maintain the strong polarization of the acid (i.e., pKa), control the size, and aid film formation and compatibility with the matrix resin. In contrast to PFOS, the new PAGs with novel organic sulfonate anions contain various functional groups that allow them to degrade by chemical or physical modes to produce relatively short fluorine containing molecules. These new PAGs are expected to be non-bioaccumalitive and environmentally friendly so as to lessen any impact on the environment and on living organisms.

The present invention is also directed to a new approach to produce environmentally friendly photoacid generators (PAGs) having anions that comprise one or more carbohydrate moieties. The photoacid generators of the invention can be formed from onium salts and various derivative compounds, for example, as illustrated by the formulas described herein.

Accordingly, the invention provides ionic PAGs, for example, an ionic PAG comprising an anion of Formula I:

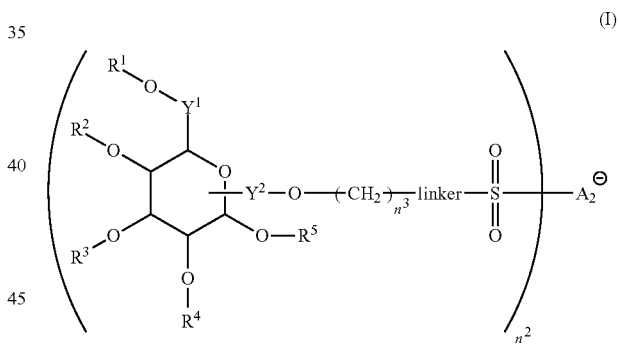

(I)

wherein
$A_2$ is O or N;
$n^2$ is 1 when $A_2$ is O and $n^2$ is 2 when $A_2$ is N;
$n^3$ is 0 to about 10;
$Y^1$ is $CH_2$ and $Y^2$ is direct bond, or $Y^1$ is direct bond and $Y^2$ is $CH_2$;
one of $R^{1-5}$ is a direct bond to the group $Y^2$ and each of the remaining $R^{1-5}$ is independently H, alkyl, cycloalkyl, heterocycle, aryl, heteroaryl, or saccharide;
linker is a diradical carbon chain comprising one to about 20 carbon atoms wherein the chain is optionally interrupted by one to five oxygen atoms, and each carbon atom is substituted with zero, one, or two halo groups, or linker is a direct bond; any alkyl, cycloalkyl, heterocycle, aryl, heteroaryl, or saccharide is optionally substituted with one to five halo, $(C_1-C_6)$alkyl, alkoxy, acyl, alkoxyacyl, acyloxy, trifluoromethyl, trifluoromethoxy, hydroxy, cyano, carboxy, nitro, oxo, or $—N(R^x)_2$ groups, wherein each $R^x$ is independently H, alkyl, aryl, acyl, or aroyl.

The invention also provides ionic PAGs, comprising an anion of Formula IA:

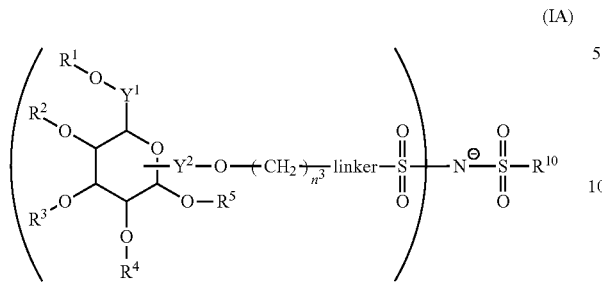
(IA)

wherein $R^{10}$ is optionally substituted alkyl, cycloalkyl, heterocycle, aryl, or heteroaryl, for example, phenyl, pyridyl, methyl, or trifluoromethyl.

The cation of the PAG can be any suitable cation, such as a cation of Formula IV:

(IV)

wherein $A_1$ is I or S; $n^1$ is 2 when $A_1$ is I, and $n^1$ is 3 when $A_1$ is S; and each $R^0$ is independently alkyl, cycloalkyl, heterocycle, aryl, or heteroaryl. The anion of Formula I and the cation of Formula IV can be combined to provide photoacid generator compound of the invention.

Certain specific anions that can be used to prepare ionic PAGs include anions of the Formula:

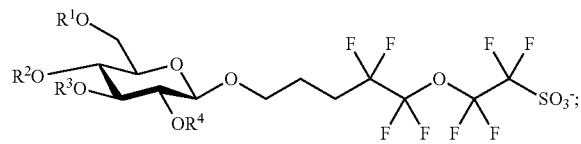

wherein each $R^{1-4}$ is independently H or a hydroxyl protecting group; and anions of the Formula:

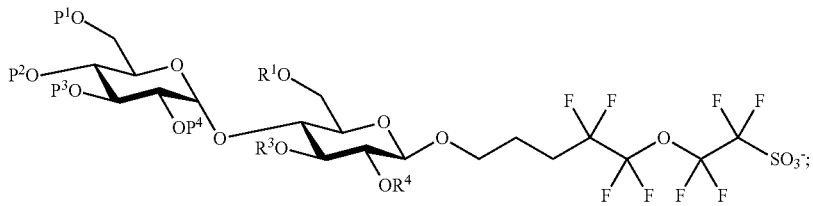

wherein each of $R^{1,3,4}$ is independently H or a hydroxyl protecting group, and each of $P^{1-4}$ is independently H or a hydroxyl protecting group.

The saccharide stereochemistry illustrated above is merely representative of two possible embodiments. Any saccharide stereochemistry can be used in various compounds and anions of the invention. For example, the monosaccharides can be derived from saccharides that have allose, altrose, glucose, mannose, gulose, idose, galactose, or talose stereochemistry, or any combination thereof, for example, when preparing disaccharide anionic compounds, non-ionic compounds, or derivatives thereof.

The invention further provides a compound of Formula II:

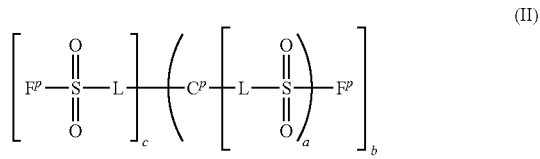
(II)

wherein
a is 1 or 2 wherein b is 1 and c is 0; or
b is 1 or 2 wherein a is 1 and c is 0; or
c is 2 and a and b are both 1;
L is O or a direct bond;
$C^p$ is an organic chromophore that includes at least one aryl, heteroaryl, heterocyclic, or carbocyclic rings containing 4 to 14 ring atoms, which optionally includes one to eight substituents, and which optionally includes a linker to an adjacent oxygen atom in Formula II, wherein the linker is an optionally substituted alkyl or =N—;

$F^p$ is a fluoroorganic group of Formula III:

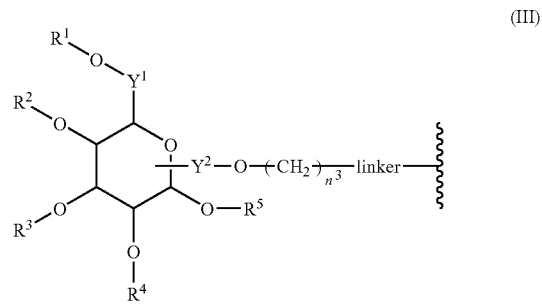
(III)

wherein
$n^3$ is 0 to about 10;
$Y^1$ is $CH_2$ and $Y^2$ is direct bond, or $Y^1$ is direct bond and $Y^2$ is $CH_2$;
each $R^0$ is independently alkyl, cycloalkyl, heterocycle, aryl, or heteroaryl;
one of $R^{1-5}$ is a direct bond to the group $Y^2$ and each of the remaining $R^{1-5}$ is independently H, alkyl, cycloalkyl, heterocycle, aryl, heteroaryl, or saccharide;

linker is a diradical carbon chain comprising one to about 20 carbon atoms wherein the chain is optionally interrupted by one to five oxygen atoms, and each carbon atom is substituted with zero, one, or two halo groups, or linker is a direct bond;

any alkyl, cycloalkyl, heterocycle, aryl, heteroaryl, or saccharide is optionally substituted with one to five halo, ($C_1$-$C_6$)alkyl, alkoxy, acyl, alkoxyacyl, acyloxy, trifluoromethyl, trifluoromethoxy, hydroxy, cyano, carboxy, nitro, oxo, or —N($R^x$)$_2$ groups, wherein each $R^x$ is independently H, alkyl, aryl, acyl, or aroyl.

For example, Formula II can have the structure of Formula IIA or IIB:

(IIA)

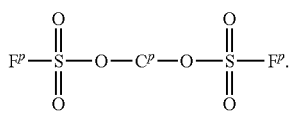

(IIB)

The invention also provides methods of preparing the compounds and compositions described herein, and certain valuable intermediates for their preparation.

The compounds of the invention can be used to prepare a chemical amplification type resist composition that includes the photoacid generator. The chemical amplification type resist composition can include a resin that changes its solubility in an alkaline developer when contacted with an acid. Other compounds can be added to the composition, for example, compounds capable of generating an acid upon exposure to radiation other than a novel PAG described herein, for example, a compound of Formula I or II. The chemical amplification type resist composition can further include a basic compound.

Additionally, the invention provides a method to form a pattern including:

a) applying a resist composition that includes a compound of Formula I or II onto a substrate to provide a substrate with a coating;

b) heat treating the coating and exposing the coating to high energy radiation or electron beam through a photo-mask; and c) optionally heat treating the exposed coating and developing the coating with a developer.

The compounds and onium salts of the present invention provide a photoacid generator for chemical amplification type resist compositions comprising the compounds or onium salts described above.

In one embodiment, the invention provides: a chemical amplification type resist composition comprising (i) a resin that changes its solubility in an alkaline developer under the action of an acid, and (ii) the aforementioned photoacid generator (PAG) that generates an acid upon exposure to radiation.

In another embodiment, the invention provides: a chemical amplification type resist composition comprising (i) a resin that changes its solubility in an alkaline developer under the action of an acid, (ii) the aforementioned photoacid generator (PAG) that generates an acid upon exposure to radiation, and (iii) a compound capable of generating an acid upon exposure to radiation, other than component (ii). The resist composition may further include (iv) a basic compound and/or (v) a carboxyl group-containing compound.

Additionally, the present invention provides a process for forming a pattern, including applying a resist composition described herein onto a substrate to form a coating; heat treating the coating and exposing the coating to high energy or electron beam through a photo-mask; optionally heat treating the exposed coating, and developing the coating with a developer.

DETAILED DESCRIPTION

Photoacid generators (PAGs) can improve resist sensitivity by decomposing to release a strong acid after absorbing a photon, followed by deprotection or crosslinking reactions catalyzed by the acid. Both ionic and nonionic PAGs include a photosensitive chromophore and an acid precursor. In the semiconductor industry, the widely used PAGs are based on acid precursors of perfluoroalkane sulfonates (PFASs), and especially perfluorooctane sulfonate (PFOS), which are known to be extremely toxic and persistent in nature.

The invention provides environmentally friendly PAGs with acidity, sensitivity, miscibility, and line edge roughness (LER) characteristics in a photoresist formulation comparable to PFAS PAGs. These new PAGs include at least one carbohydrate moiety, rendering them significantly more environmentally friendly than PFASs. The invention includes the design and preparation of a series of ionic and nonionic PAGs, some of which are specifically directed to 248 nm and 193 nm lithography (including immersion lithography), and EUV lithography. The incorporation of saccharide groups, for example, monosaccharide groups, allows for the control of acid size and volatility while maintaining acid strength. Thermal and absorption properties can be controlled by balancing the composition of elements.

The EPA has regulated and prohibited the use of PFOS for many industries because of their toxic and persistent nature. Although the semiconductor industry is currently still excused from some of these regulations, the search for alternative environmentally friendly candidates has been ongoing in the industry for many years. Accordingly, environmentally friendly PAGs are eagerly sought by the industrial community.

The PAGs of the invention are environmentally benign, and are therefore commercially attractive due to the low costs and wide availability of saccharide compounds. The sweet PAGs have been found to have favorable performance characteristics for various types of lithography, including 193 nm lithography.

DEFINITIONS

The following definitions are provided to help describe and clarify the invention. Specific values listed below for radicals, substituents, and ranges, are for illustration only; they do not exclude other defined values or other values within defined ranges for the radicals and substituents. Generic terms include each of their species, for example, the term halo includes and can explicitly be fluoro, chloro, bromo, or iodo.

The term "about" refers to a value that is greater than or less than the specified value by 5%, 10%, or 25%. The term "about" can also refer to a value that is greater than or less than the specified value by one or two integers. The phrase "one or more" is readily understood by one of skill in the art, particularly when read in context of its usage. For example, one or more substituents on a phenyl ring refers to one to five, or one to up to four, for example if the phenyl ring is disubstituted.

Specific values listed below for radicals, substituents, and ranges, are for illustration only; they do not exclude other defined values or other values within defined ranges for the radicals and substituents.

It will be appreciated that the compounds of the invention can contain asymmetrically substituted carbon atoms, and can be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomeric form is specifically indicated.

Only stable compounds are contemplated by and employed in the present invention. "Stable compound" and "stable structure" are meant to indicate a compound that is sufficiently robust to survive isolation to a useful degree of purity from a reaction mixture, and survive formulation into an effective PAG.

The term "alkyl" refers to a branched, unbranched, or cyclic hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., an alkylene).

The term "alkenyl" refers to a monoradical branched or unbranched partially unsaturated hydrocarbon chain (i.e. a carbon-carbon, sp$^2$ double bond) preferably having from 2 to 10 carbon atoms, preferably 2 to 6 carbon atoms, and more preferably from 2 to 4 carbon atoms. Examples include, but are not limited to, ethylene or vinyl, allyl, cyclopentenyl, and 5-hexenyl. The alkenyl can be unsubstituted or substituted.

The term "alkynyl" refers to a monoradical branched or unbranched hydrocarbon chain, having a point of complete unsaturation (i.e. a carbon-carbon, sp triple bond), preferably having from 2 to 10 carbon atoms, preferably 2 to 6 carbon atoms, and more preferably from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, and the like. The alkynyl can be unsubstituted or substituted.

"Alkylene" refers to a saturated, branched or straight chain hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like. The alkynyl can be unsubstituted or substituted.

"Alkenylene" refers to an unsaturated, branched or straight chain hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—). The alkenylene can be unsubstituted or substituted.

"Alkynylene" refers to an unsaturated, branched or straight chain hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH$_2$C≡C—), and 4-pentynyl (—CH$_2$CH$_2$CH$_2$C≡CH—). The alkynylene can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "aryl" refers to an aromatic hydrocarbon group derived from the removal of one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "halo" refers to fluoro, chloro, bromo, and iodo. Similarly, the term "halogen" refers to fluorine, chlorine, bromine, and iodine.

Substituted alkyl groups include haloalkyl groups. The term "haloalkyl" refers to alkyl as defined herein substituted by 1-4 halo groups, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, perfluorooctyl, and the like.

The term "heteroaryl" can be defined as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, selected from alkyl, alkenyl, alkynyl, alkoxy, halo, haloalkyl, hydroxy, hydroxyalkyl, aryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl and cyano. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The term "heterocycle" includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include, by way of example and not limitation: pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 7 carbon atoms as a monocycle, 7 to 12 carbon atoms as a bicycle, and up to about 30 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl, adamantly, and naphthyl.

The terms "cycloalkylene", "carbocyclene", "arylene", "heterocyclene", and "heteroarylene" refer to diradicals of the parent group. For example, "arylene" refers to an aryl diradical, e.g., an aryl group that is bonded to two other groups or moieties.

The terms "acyl" and "alkanoyl" refer to groups of the formula —C(=O)R, wherein R is an alkyl group as previously defined. The term "aroyl" refers to groups of the formula —C(=O)Ar, wherein Ar is an aryl group as previously defined.

The term "alkoxycarbonyl" refers to groups of the formula —C(=O)OR, wherein R is an alkyl group as previously defined.

The term "alkoxyacyl" refers to groups of the formula —C(=O)R—OR, wherein R is alkyl as previously defined. Example of alkoxyacyl groups include methoxyacetyl and ethoxyacetyl.

The term "acyloxy" refers to groups of the formula —O—C(=O)R, wherein R is an alkyl group as previously defined.

The term "amino" refers to —NH$_2$, and the term "alkylamino" refers to —NR$_2$, wherein at least one R is alkyl and the second R is alkyl or hydrogen. The term "acylamino" refers to RC(=O)NH—, wherein R is alkyl or aryl.

The term "saccharide" refers to a sugar or sugar moiety, for example, a monosaccharide, a disaccharide, an oligosaccharide, or a polysaccharide. Typically a saccharide refers to a monosaccharide such as such as allose, altrose, glucose, mannose, gulose, idose, galactose, or talose. A saccharide can include hydroxyl protecting groups such as, but not limited to, acetyl groups, benzyl groups, benzylidene groups, silyl groups, methoxy ether groups, or combinations thereof. The saccharide groups can also be in pyranose form, furanose form, or linear form.

A saccharide can be linked to another group, such as a carbon chain or linker, using commonly known techniques of the art. Linking a saccharide to an other group forms a glycoside. For example, glycosides can be formed by reacting mono-, di-, tri- or polysaccharides with sufficiently reactive group of another compound. Suitable saccharide starting materials can include a halogen or methoxy group at an anomeric position, or a leaving group on a hydroxyl group. Saccharides can include, for example, glucose, glucuronic acid, mannose, galactose, sorbase, ribose, maltose, sucrose, modified cellulosics, dextrans, modified starches and the like. Compounds linked to a saccharide can advantageously exhibit improved water solubility compared to a compound prior to linking to the saccharide. Glycoside derivatives can be prepared by glycosylation techniques well know in the art, for example, as described in PCT Applications WO 96/34005 (Danishefsky et al.) and 97/03995 (Danishefsky et al.).

The term "substituted" is intended to indicate that one or more (e.g., 1, 2, 3, 4, or 5; in some embodiments 1, 2, or 3; and in other embodiments 1 or 2) hydrogen atoms on the group indicated in the expression using "substituted" is replaced with a "substituent", which can be a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl(alkyl)amine, and cyano. Additionally, the suitable indicated groups can include, e.g., —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR —S(=O)$_2$O⁻, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for the substituted group.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

Compounds can be prepared by contacting two or more starting materials under appropriate reaction conditions, sometimes in the presence of certain reagents, for example, an acid, a base, an oxidant, or a reductant. The term "contacting" refers to the act of touching, making contact, or of bringing to immediate or close proximity, including at the molecular level, for example, to bring about a chemical reaction.

Protecting Groups

The term "protecting group" refers to any group which, when bound to a hydroxyl, nitrogen, or other heteroatom prevents undesired reactions from occurring at this group and which can be removed by conventional chemical or enzymatic steps to reestablish the 'unprotected' hydroxyl, nitrogen, or other heteroatom group. The particular removable group employed is often interchangeable with other groups in various synthetic routes. Certain removable protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Greene describes many nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J.; *Protecting Groups* (Georg Thieme Verlag Stuttgart, New York, 1994), which is incorporated herein by reference in its entirety. Some specific protecting groups that can be employed in conjunction with the methods of the invention are discussed below.

Typical hydroxyl and nitrogen protecting groups described in Greene (pages 14-118) include benzyl ethers, silyl ethers, esters including sulfonic acid esters, carbonates, sulfates, and sulfonates. For example, suitable protecting groups can include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate (mesitoate)); carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3-tetramethylbutyl)phenoxyacetate, 2,4-bis(1,1-dimethylpropyl)-phenoxyacetate, chlorodiphenylacetate, isobutyrate, monosuccinate, (E)-2-methyl-2-butenoate (tigloate), o-(methoxycarbonyl)benzoate, p-poly-benzoate, α-naphthoate, nitrate, alkyl N,N,N',N'-tetramethyl-phosphorodiamidate, n-phenylcarbamate, borate, 2,4-dinitrophenylsulfenate); and sulfonates (sulfate, methanesulfonate (mesylate), benzylsulfonate, tosylate, triflate).

Resist Compositions

Upon use of a chemical amplification type positive-working resist compositions, a resist film is formed by dissolving a resin having acid labile groups as a binder and a compound capable of generating an acid upon exposure to radiation ("a photoacid generator") in a solvent system, applying the resist solution onto a substrate by a variety of methods, and evaporating off the solvent, optionally by heating, to provide a resist film. A solvent system is any solvent or combination of solvents that can dissolve a photoacid generator of interest. The resist film is then exposed to radiation, for example, deep UV radiation, through a mask of a predetermined pattern. This is optionally followed by post-exposure baking (PEB) for promoting acid-catalyzed reaction. The exposed resist film is developed with an aqueous alkaline developer for removing the exposed area of the resist film, obtaining a positive pattern profile. The substrate is then etched by any desired technique. Finally, the remaining resist film is removed by dissolution in a remover solution or washing, leaving the substrate having the desired pattern profile.

Chemical amplification type positive-working resist compositions adapted for KrF excimer lasers generally use a phenolic resin, for example, polyhydroxy-styrene, in which some or all of the hydrogen atoms of phenolic hydroxyl groups are protected with acid labile protective groups. Onium salts, such as iodonium salts and sulfonium salts having perfluorinated anions, are typically used as the photoacid generator. If desired, the resist compositions can contains one or more additives, for example, a dissolution inhibiting or promoting compound in the form of a carboxylic acid and/or phenol derivative having a molecular weight of up to about 3,000, in which some or all of the hydrogen atoms of carboxylic acid and/or phenolic hydroxyl groups are protected with acid labile groups, a carboxylic acid compound for improving dissolution characteristics, a basic compound for improving contrast, and a surfactant for improving coating characteristics.

Ionic photoacid generators, typically onium salts, can be advantageously used as the photoacid generator in chemical amplification type resist compositions, especially chemical amplification type positive-working resist compositions adapted for KrF excimer lasers. Ionic photoacid generators provide a high sensitivity and resolution and are free from storage instability.

Reference to a compound of Formula I refers to a compound derived from an anion of Formula I and a suitable cation, such as, but not limited to, a cation of Formula IV. A compound of Formula I or II can be used as a photoacid generator in a resist material, especially chemical amplification type resist materials. Accordingly, the invention provides resist compositions comprising a compound of one of Formulas I-II as the photoacid generator. The resist compositions may be either positive- or negative-working. The resist compositions of the invention include a variety of embodiments, including one or more of any of the following, in any combination:

1) a chemically amplified positive working resist composition comprising (A) a resin that changes its solubility in an alkaline developer under the action of an acid, (B) a photoacid generator comprising a compound of one of Formulas I-II capable of generating an acid upon exposure to radiation, and (C) an organic solvent;

2) a chemically amplified positive working resist composition of 1) above further comprising (D) a photoacid generator capable of generating an acid upon exposure to radiation other than component (B);

3) a chemically amplified positive working resist composition of 1) or 2) further comprising (E) a basic compound;

4) a chemically amplified positive working resist composition of 1) to 3) further comprising (F) an organic acid derivative;

5) a chemically amplified positive working resist composition of 1) to 4) further comprising (G) a compound with a molecular weight of up to about 3,000 that changes its solubility in an alkaline developer under the action of an acid;

6) a chemically amplified negative working resist composition comprising (B) a photoacid generator comprising a compound of one of Formulas I-II capable of generating an acid upon exposure to radiation, (H) an alkali-soluble resin, an acid crosslinking agent capable of forming a crosslinked structure under the action of an acid, and (C) an organic solvent;

7) a chemically amplified negative working resist composition of 6) further comprising (D) another photoacid generator;

8) a chemically amplified negative working resist composition of 6) or 7) further comprising (E) a basic compound; as well as 9) a chemically amplified negative working resist composition of 6), 7) or 8) further comprising (J) an alkali-soluble compound with a molecular weight of up to about 2,500, up to about 5,000, or up to about 10,000.

Additionally, the invention provides a process for forming a pattern, comprising the steps of applying a resist composition described above onto a substrate to form a coating; heat treating the coating and exposing the coating to high energy radiation (for example, with a wavelength of up to 300 nm) or electron beam through a photo-mask; optionally heat treating the exposed coating, and developing the coating with a developer.

Various components of the compositions of the invention include the following:

Component (A): Resin

Component (A) is a resin which changes its solubility in an alkaline developer solution under the action of an acid. It is preferably, though not limited thereto, an alkali-soluble resin having phenolic hydroxyl and/or carboxyl groups in which some or all of the phenolic hydroxyl and/or carboxyl groups are protected with acid-labile protective groups.

The alkali-soluble resins having phenolic hydroxyl and/or carboxyl groups include homopolymers and copolymers of p-hydroxystyrene, m-hydroxystyrene, α-methyl-p-hydroxystyrene, 4-hydroxy-2-methylstyrene, 4-hydroxy-3-methylstyrene, methacrylic acid, and acrylic acid. Also included are copolymers in which units free of alkali-soluble sites such as styrene, α-methylstyrene, acrylate, methacrylate, hydrogenated hydroxystyrene, maleic anhydride and maleimide are introduced in addition to the above-described units in such a proportion that the solubility in an alkaline developer is not be extremely reduced. Substituents on acrylates and methacrylates may be any substituent that does not undergo acidolysis. In one embodiment, the substituents are straight, branched or cyclic ($C_1$-$C_8$)alkyl groups and aromatic groups such as aryl groups, but not limited thereto. In other specific embodiments, the substituents can be methyl, ethyl, propyl (normal or iso), butyl (normal or iso), cyclohexyl, etc., or combinations thereof.

Non-limiting examples of alkali-soluble resins are given below. These polymers may also be used as the material from which the resin (A) (which changes its solubility in an alkaline developer under the action of an acid) is prepared. These polymers may also be used as the alkali-soluble resin that serves as component (H), described hereinbelow. Examples include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxy-styrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers, as well as dendritic and hyperbranched polymers thereof, but are not limited to these combinations.

The alkali-soluble resins or polymers should preferably have a weight average molecular weight (Mw) of about 3,000 to about 100,000. Many polymers with Mw of less than about 3,000 do not perform well in heat resistance and film formation. Many polymers with Mw of more than about 100,000 give rise to problems with respect to dissolution in the resist solvent and developer. The polymer can have a dispersity (Mw/Mn) of up to about 3.5, and more preferably up to about 1.5. With a dispersity of more than about 3.5, resolution is sometimes lower than is desired. Although the preparation method is not critical, a poly(p-hydroxystyrene) or similar polymer with a low dispersity or narrow dispersion can be synthesized by controlled free radical or living anionic polymerization.

The resin (A) can be an alkali-soluble resin having hydroxyl or carboxyl groups, some of which are replaced by acid labile groups such that the solubility in an alkaline developer changes as a result of severing of the acid labile groups under the action of an acid generated by the photoacid generator upon exposure to radiation.

In the chemical amplification type resist composition, an appropriate amount of (B) the photoacid generator comprising an a compound of one of Formulas I-II added is from about 0.5 part to about 20 parts by weight, and typically from about 1 to about 10 parts by weight, per 100 parts by weight of the solids in the composition. The photoacid generators may be used alone or as admixture of two or more types. The transmittance of the resist film can be controlled by using a photoacid generator having a low transmittance at the exposure wavelength and adjusting the amount of the photoacid generator added.

Component B: Photoacid Generator Compounds (PAGs)

A photoacid generator compound of the invention can include any one of Formulas I-VI described herein. Several general and specific examples of useful PAGs are described and illustrated in the Examples section. The PAGs can be non-ionic compounds, or ionic compounds, for example, one that includes an anion of Formula I.

A specific value of $A_2$ is O. Another specific value of $A_2$ is N.

A specific value of $n^2$ is 1 when $A_2$ is O. Another specific value of $n^2$ is 2 when $A_2$ is N.

Specific values of $n^3$ include 0, 1, 2, 3, 4, 5, 6, 7, 8, 9, 10, 11, and 12. In one specific embodiment, $n^3$ is 3.

A specific value for $Y^1$ is $CH_2$ and $Y^2$ is direct bond. Another specific value for $Y^1$ is a direct bond and $Y^2$ is $CH_2$.

In Formula I, one of $R^{1-5}$ will always be a direct bond to the group $Y^2$. Thus, the saccharide moiety can be linked to the remaining portion of the anion of Formula I at any carbon atom of the saccharide. For example, in one embodiment, $R^5$ is a direct bond to $Y^2$. In another embodiment, $R^4$ is a direct bond to $Y^2$. In another embodiment, $R^3$ is a direct bond to $Y^2$. In another embodiment, $R^2$ is a direct bond to $Y^2$, and in another embodiment, $R^1$ is a direct bond to $Y^2$.

Each of the remaining $R^{1-5}$ can independently be a variety of groups, including H, alkyl, cycloalkyl, heterocycle, aryl, heteroaryl, and saccharide, each of which can be optionally substituted. In some embodiments, each of $R^{1-5}$ are H. In other embodiments, some of $R^{1-5}$ can H and others can be various groups, such as protecting groups, as described above. In one embodiment, each of $R^{1-5}$ that are not directly bonded to the group $Y^2$ are acetyl. In other embodiments, three of $R^{1-5}$ that are not directly bonded to the group $Y^2$ are H or acetyl, and one is a saccharide, thus forming a disaccharide moiety.

The group "linker" can be a diradical carbon chain comprising one to about 20 carbon atoms wherein the chain is optionally interrupted by one to five oxygen atoms, and each carbon atom is substituted with zero, one, or two halo groups, or linker is a direct bond. Suitable linkers include divalent radicals of the formula W-A-W wherein A is $(C_1-C_6)$alkyl, $(C_2-C_6)$alkenyl, $(C_2-C_6)$alkynyl, $(C_3-C_8)$cycloalkyl, or $(C_6-C_{10})$aryl, and each W is —N(R)C(=O)—, —C(=O)N(R)—, —OC(=O)—, —C(=O)O—, —O—, —S—, —S(O)—, —S(O)_2—, —N(R)—, —C(=O)—, or a direct bond; and each R is independently H or $(C_1-C_6)$alkyl. In some embodiments, at least one carbon of linker is substituted with two fluoro groups or linker is a direct bond. In some embodiments, the linker comprises —C(CF_3)_2—, —(CF_2)—O—(CF_2)_2—O—(CF_2)—, —(CF_2)_2—O—(CF_2)_2—, —(CF_2)_n— wherein n is 1 to about 6, or a direct bond.

Any group such as alkyl, cycloalkyl, heterocycle, aryl, heteroaryl, or saccharide can be substituted with one or more, for example, 1-5, halo, $(C_1-C_6)$alkyl, alkoxy, acyl, alkoxyacyl, acyloxy, trifluoromethyl, trifluoromethoxy, hydroxy, cyano, carboxy, nitro, oxo, or —N(R^x)_2 groups, wherein each $R^x$ is independently H, alkyl, aryl, acyl, or aroyl.

In one embodiment, the anion can be

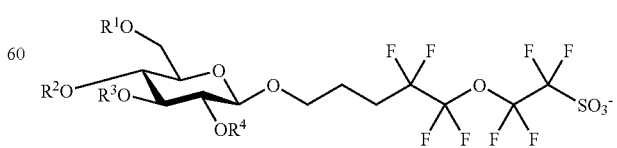

wherein each $R^{1-4}$ is independently H or a hydroxyl protecting group.

In another embodiment, the anion can be

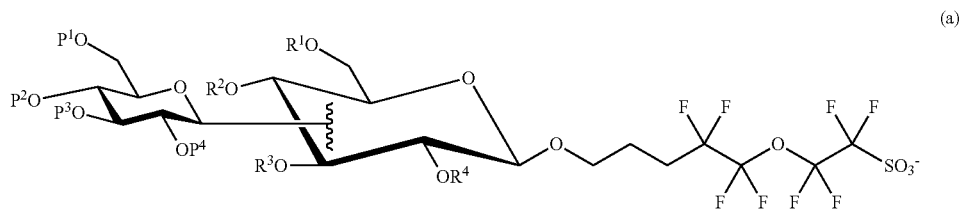

wherein one $R^{1-4}$ group is a direct bond to the anomeric carbon of saccharide (a), the other $R^{1-4}$ groups are each independently H or hydroxyl protecting groups, and each $P^{1-4}$ is independently H or a hydroxyl protecting group.

In another embodiment, the anion can be

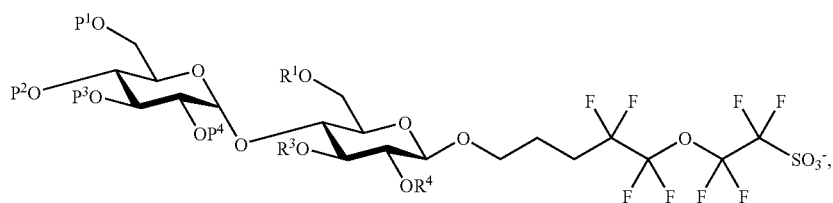

wherein each of $R^{1,3,4}$ is independently H or a hydroxyl protecting group, and each of $P^{1-4}$ is independently H or a hydroxyl protecting group. For each of the above illustrated anions, the stereochemistry is representative of certain specific embodiments and other saccharide stereochemistries, including allose, altrose, glucose, mannose, gulose, idose, galactose, or talose stereochemistry, or any combination thereof, can be employed in the anions and compounds of the invention.

Compounds of the invention can include an anion as described above and a cation of Formula IV. A specific value of $A_1$ is I. Another specific value of $A_1$ is S. A specific value of $n^1$ is 2 when $A_1$ is I. Another specific value of $n^1$ is 3 when $A_1$ is S. Each $R^0$ can be independently alkyl, cycloalkyl, heterocycle, aryl, or heteroaryl. In one embodiment, $R^0$ is aryl or heteroaryl. In one specific embodiment, each $R^0$ is phenyl.

Other PAGs include compounds of Formula II. A specific value of a is 1. Another specific value of a is 2. A specific value of b is 1. Another specific value of b is 2. A specific value of c is 0. Another specific value of c is 2.

A specific value of $C^p$ is a monovalent imide or a divalent diimide. Another specific value of $C^p$ is a mono- or divalent benzene moiety, such as a divalent nitrobenzene. The group $C^p$ can be substituted with one or more, for example, one to about eight, substituents as defined above.

In one embodiment, Formula II can have the structure of Formula IIA:

(IIA)

In another embodiment, Formula II can have the structure of Formula IIB:

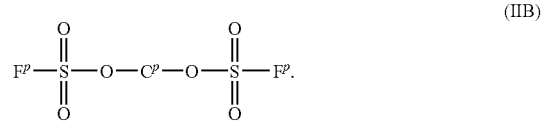

(IIB)

In one embodiment, $C^p$ can be one or more of:

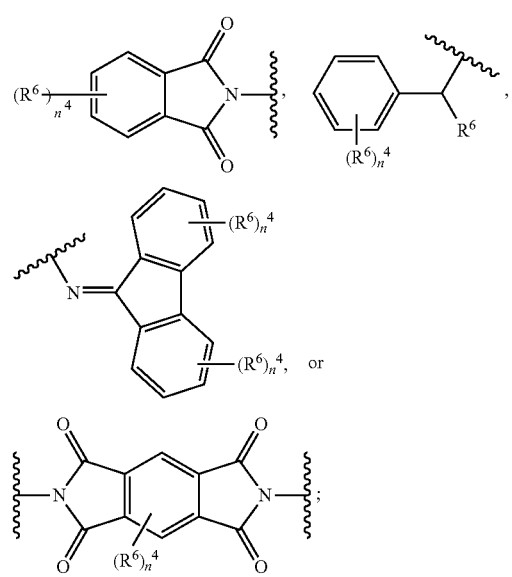

wherein $n^4$ can be 1-5. Each $R^6$ can be independently H, alkyl, cycloalkyl, heterocycle, aryl, heteroaryl, halo, $(C_1-C_6)$alkyl, alkoxy, acyl, alkoxyacyl, acyloxy, trifluoromethyl, trifluoromethoxy, hydroxy, cyano, carboxy, nitro, oxo, or —N(R$^x$)$_2$ groups, wherein each Rx is independently H, alkyl, aryl, acyl, or aroyl.

In one embodiment, Formula III is:

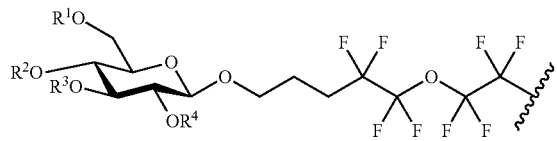

wherein each R$^{1-4}$ is independently H or a hydroxyl protecting group.

In another embodiment, Formula III is:

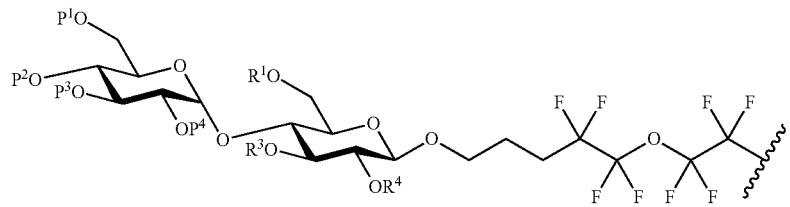

wherein each of R$^{1,3,4}$ is independently H or a hydroxyl protecting group, and each of P$^{1-4}$ is independently H or a hydroxyl protecting group.

The invention also includes a PAG of Formula II that has the formula:

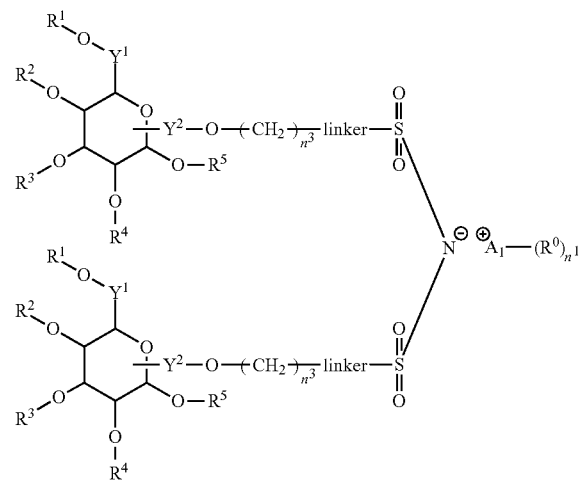

wherein each variable is as defined above.

Component (C): Solvent

Component (C) can be an organic solvent. Illustrative, non-limiting examples include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methyl pyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methylpyrrolidone, dimethylsulfoxide, γ-butyrolactone, propylene glycol methyl ether acetate, propylene glycol ethyl ether acetate, propylene glycol propyl ether acetate, methyl lactate, ethyl lactate, propyl lactate, and tetramethylene sulfone. In one embodiment, the propylene glycol alkyl ether acetates and alkyl lactates are used in the compositions of the invention.

The alkyl groups of the propylene glycol alkyl ether acetates can be of 1 to about 4 carbon atoms, for example, methyl, ethyl and propyl. Propylene glycol alkyl ether acetates include 1,2- and 1,3-substituted derivatives and each includes up to about three isomers, depending on the combination of substituted positions, which may be used alone or in admixture. The alkyl groups of the alkyl lactates can be of 1 to 4 carbon atoms, for example, methyl, ethyl and propyl. These solvents may be used alone or in admixture. In one embodiment, a useful solvent system is a mixture of a propylene glycol alkyl ether acetate and an alkyl lactate. The mixing ratio of the propylene glycol alkyl ether acetate and the alkyl lactate can be a mixture of about 50 to about 99 parts by weight of the propylene glycol alkyl ether acetate with about 50 to about 1 part by weight of the alkyl lactate. The solvent mixture of the propylene glycol alkyl ether acetate and the alkyl lactate may further contain one or more other solvents.

Component (D): Additional Photoacid Generator Compound

In one embodiment, the resist composition further contains component (D), a compound capable of generating an acid upon exposure to high energy radiation, that is, a second photoacid generator other than the photoacid generator (B). The second photoacid generators include sulfonium salts and iodonium salts as well as sulfonyldiazomethane, N-sulfonyloxyimide, benzoinsulfonate, nitrobenzylsulfonate, sulfone, and glyoxime derivatives. They may be used alone or in admixture of two or more. Preferred component (D) photoacid generators used herein are sulfonium salts and iodonium salts.

In the resist composition comprising (B), a compound of one of formulas I-II, as the first photoacid generator, an appropriate amount of the second photoacid generator (D) is 0 to about 20 parts, and especially about 1 to about 10 parts by weight per 100 parts by weight of the solids in the composition. The second photoacid generators may be used alone or in admixture of two or more. The transmittance of the resist film can be controlled by using a (second) photoacid generator having a low transmittance at the exposure wavelength and adjusting the amount of the photoacid generator added.

Component (E): Base

The basic compound used as component (E) can be a compound capable of suppressing the rate of diffusion when the acid generated by the photoacid generator diffuses within the resist film. The inclusion of this type of basic compound holds down the rate of acid diffusion within the resist film, resulting in better resolution. In addition, it can suppress changes in sensitivity following exposure and can reduce substrate and environment dependence, as well as improve the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, imide derivatives, and combinations thereof.

The basic compounds may be used alone or in admixture of two or more. The basic compound is preferably formulated in an amount of 0 to about 2 parts, and especially about 0.01 to about 1 part by weight, per 100 parts by weight of the solids in the resist composition. The use of more than about 2 parts of the basis compound can result in a low sensitivity.

Component (F)

Illustrative examples of the organic acid derivatives (F) include, but are not limited to, organic acid derivatives including 4-hydroxyphenylacetic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxy-phenyl)valeric acid, 4-tert-butoxyphenylacetic acid, 4-(4'-hydroxyphenyl)butyric acid, 3,4-dihydroxymandelic acid, 4-hydroxymandelic acid, and combinations thereof. In certain embodiments, salicylic acid and 4,4-bis(4'-hydroxyphenyl)valeric acid are employed. They may be used alone or in admixture of two or more.

In the resist composition comprising a compound of one of Formulas I-II, the organic acid derivative can be formulated in an amount of up to about 5 parts, and especially up to about 1 part by weight, per 100 parts by weight of the solids in the resist composition. The use of more than about 5 parts of the organic acid derivative can result in a low resolution. Depending on the combination of the other components in the resist composition, the organic acid derivative may be omitted.

Component (G): Dissolution Inhibitor

In one preferred embodiment, the resist composition further contains (G) a compound with a molecular weight of up to about 3,000 which changes its solubility in an alkaline developer under the action of an acid, e.g., a dissolution inhibitor. Typically, a compound obtained by partially or entirely substituting acid labile substituents on a phenol or carboxylic acid derivative having a molecular weight of up to about 2,500 is added as the dissolution inhibitor.

In the resist composition comprising a compound of one of Formulas I-II, an appropriate amount of the dissolution inhibitor (G) is up to about 20 parts, and especially up to about 15 parts by weight per 100 parts by weight of the solids in the composition. With more than about 20 parts of the dissolution inhibitor, the resist composition becomes less heat resistant because of an increased content of monomer components.

Component (H): Alkali-Soluble Resin

Component (B), a compound of one of Formulas I-II, can also be used in a chemical amplification negative-working resist composition. This composition further contains an alkali-soluble resin as component (H), examples of which are described above in the description of component (A), though the alkali-soluble resins are not limited thereto.

In various embodiments, the alkali-soluble resin can be poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers, a dendritic and/or hyperbranched polymer of the foregoing polymers, or combinations thereof.

The alkali-soluble resin polymer can have a weight average molecular weight (Mw) of about 3,000 to about 100,000. Many polymers with Mw of less than about 3,000 do not perform well in heat resistance and film formation. Many polymers with Mw of more than 100,000 give rise to problems with respect to dissolution in the resist solvent and developer. The polymer can have a dispersity (Mw/Mn) of up to about 3.5, and more preferably up to about 1.5. With a dispersity of more than about 3.5, resolution is sometimes lower than is desired. Although the preparation method is not critical, a poly(p-hydroxystyrene) or similar polymer with a low dispersity or narrow dispersion can be synthesized by controlled free radical or living anionic polymerization.

To impart a certain function, suitable substituent groups can be introduced into some of the phenolic hydroxyl and carboxyl groups on the acid labile group-protected polymer. Various embodiments include substituent groups for improving adhesion to the substrate, substituent groups for improving etching resistance, and especially substituent groups that are relatively stable against acid and alkali and are effective for controlling dissolution rate such that the dissolution rate in an alkali developer of unexposed and low exposed areas of a resist film does not increase to an undesirable level. Illustrative non-limiting substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, iso-propyl, n-butyl, sec-butyl, acetyl, pivaloyl, adamantyl, isobornyl, and cyclohexyl. It is also possible to introduce acid-decomposable substituent groups such as t-butoxycarbonyl and relatively acid-undecomposable substituent groups such as t-butyl and t-butoxycarbonylmethyl.

An acid crosslinking agent capable of forming a crosslinked structure under the action of an acid is also contained in the negative resist composition. Typical acid crosslinking agents are compounds having at least two hydroxymethyl, alkoxymethyl, epoxy or vinyl ether groups in a molecule. Substituted glycoluril derivatives, urea derivatives, and hexa(methoxymethyl)melamine compounds are suitable as the acid crosslinking agent in the chemically amplified negative-resist composition comprising the photoacid generators described herein. Examples of acid crosslinking agents include N,N,N',N'-tetramethoxymethylurea, hexamethoxymethylmelamine, tetraalkoxymethyl-substituted glycoluril compounds such as tetrahydroxymethyl-substituted glycoluril and tetramethoxy-methylglycoluril, and condensates of phenolic compounds such as substituted or unsubstituted bis(hydroxymethylphenol) compounds and bisphenol A with epichlorohydrin. In certain specific embodiments, the acid crosslinking agent can be one or more of 1,3,5,7-tetraalkoxy-methylglycolurils such as 1,3,5,7-tetramethoxymethylglycoluril, 1,3,5,7-tetrahydroxymethylglycoluri-1,2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine. In the resist composition, an appropriate amount of the acid crosslinking agent is about 1 to about 25 parts, and especially about 5 to about 15 parts by weight per 100 parts by weight of the solids in the composition. The acid crosslinking agents may be used alone or in admixture of two or more.

Component (J): Low Molecular Weight Alkali-Soluble Compound

Component (J), an alkali-soluble compound having a molecular weight of up to about 2,500 can be blended into the chemical amplification type negative-working resist composition. The compound should preferably have at least two phenol and/or carboxyl groups. Illustrative non-limiting examples include cresol, catechol, resorcinol, pyrogallol, fluoroglycin, bis(4-hydroxyphenyl)methane, 2,2-bis(4'-hydroxyphenyl)-propane, bis(4-hydroxyphenyl)sulfone, 1,1,1-tris(4'-hydroxyphenyl)ethane, 1,1,2-tris(4'-hydroxyphenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)propionic acid, 2,5-dihydroxyphenylacetic acid, 3,4-dihydroxy-phenylacetic acid, 1,2-phenylenediacetic acid, 1,3-phenylenediacetic acid, 1,4-phenylene-diacetic acid, 1,2-phenylenedioxydiacetic acid, 1,4-phenylenedipropanoic acid, benzoic acid, salicylic acid, 4,4-bis(4'-hydroxyphenyl) valeric acid, 4-tert-butoxyphenylacetic acid, 4-(4-hydroxyphenyl)butyric acid, 3,4-dihydroxymandelic acid, and 4-hydroxymandelic acid. In certain specific embodiments, component (J) is salicylic acid and/or 4,4-bis(4'-hydroxyphenyl)valeric acid. The compounds can be used alone or in admixture of two or more. The addition amount can be 0 to about 20 parts, preferably about 2 to about 10 parts by weight per 100 parts by weight of the solids in the composition.

Additional Optional Components

In the resist composition according to the invention, there may be additional additives such as a surfactant for improving coating, and/or a light absorbing agent for reducing diffuse reflection from the substrate.

Illustrative non-limiting examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products K.K.), Megaface F171, F172 and F173 (Dai-Nippon Ink & Chemicals K.K.), Florade FC430 and FC431 (Sumitomo 3M K.K.), Asahiguard AG710, Surflon S-381, S-382, SC101, SC102, SC103, SC104, SC105, SC106, Surfynol E1004, KH-10, KH-20, KH-30 and KH-40 (Asahi Glass K.K.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo K.K.). In certain specific embodiments, FC430, Surflon S-381 and Surfynol E1004 are employed. These surfactants may be used alone or in combination with others.

In the resist composition, the surfactant can be formulated in an amount of up to about 2 parts, and especially up to about 1 part by weight, per 100 parts by weight of the solids in the resist composition.

A UV absorber can be added to the resist composition. An appropriate amount of UV absorber blended is 0 to about 10 parts, more preferably about 0.5 to about 10 parts, most preferably about 1 to about 5 parts by weight per 100 parts by weight of the base resin.

For the microfabrication of integrated circuits, any well-known lithography may be used to form a resist pattern from the chemical amplification positive- or negative-working resist composition.

Substrates

The composition can be applied to a substrate (e.g., Si, $SiO_2$, SiN, SiON, TiN, WSi, BPSG, SOG, organic anti-reflecting film, etc.) by a suitable coating technique such as spin coating, roll coating, flow coating, dip coating, spray coating or doctor coating. The coating can be prebaked on a hot plate at a temperature of about 60° C. to about 150° C. for about 1 to about 10 minutes, typically about 80° C. to about 120° C. for about 1 to 5 minutes. The resulting resist film is generally about 0.1 to about 2.0 μm thick. With a mask having a desired pattern placed above the resist film, the resist film can then be exposed to actinic radiation, typically having an exposure wavelength of up to about 300 nm, such as UV, deep-UV, electron beams, x-rays, excimer laser light, γ-rays or synchrotron radiation in an exposure dose of about 1 to 200 $mJ/cm^2$, typically about 10 to 100 $mJ/cm^2$. The film can be further baked on a hot plate at about 60° C. to about 150° C. for about 1 to 5 minutes, typically about 80° C. to about 120° C. for about 1 to 3 minutes (post-exposure baking=PEB).

Thereafter the resist film can be developed with a developer in the form of an aqueous base solution, for example, about 0.1% to about 5%, typically about 2% to about 3% aqueous solution of tetramethylammonium hydroxide (TMAH) for about 0.1 to 3 minutes, typically about 0.5 to about 2 minutes by conventional techniques such as dipping, puddling, or spraying. In this way, a desired resist pattern can be formed on the substrate. It is appreciated that the resist composition of the invention is well suited for micro-patterning using such actinic radiation as deep UV with a wavelength of about 254 nm to about 193 nm, 13.4 nm (EUV), electron beams, x-rays, excimer laser light, y-rays and/or synchrotron radiation. With any of the above-described parameters outside the above-described range, the process may sometimes fail to produce the desired pattern.

General Synthetic Procedures for Photoacid Generator Compounds

The useful PAGs described herein can be prepared as outlined below in the Examples and by using techniques and reaction sequences known to those of skill in the art of organic synthesis. Many of the techniques are elaborated in standard texts such as *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis, Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

It is appreciated that those of skill in synthetic organic chemistry understand that reagents can be referred to by their chemical names or formulas that represent their structures prior to addition to a chemical reaction mixture, even though the chemical species actually present in the reaction mixture or involved in the reaction may be otherwise. While a compound may undergo conversion to a compound bearing a different name or represented by a different formula prior to or during a specified reaction step, reference to these compounds by their original name or formula is acceptable and is well-understood by those of skill in the art of organic chemistry.

Obviously, numerous modifications and variations of the present invention are possible in light of the above teachings. It is therefore to be understood that within the scope of the appended claims, the invention may be practiced otherwise than as specifically described herein. Specific ranges, values, and embodiments provided below are for illustration purposes only and do not otherwise limit the scope of the invention, as defined by the claims.

The invention also provides useful intermediates for preparing the PAGs of the invention, for example, compounds of Formula V:

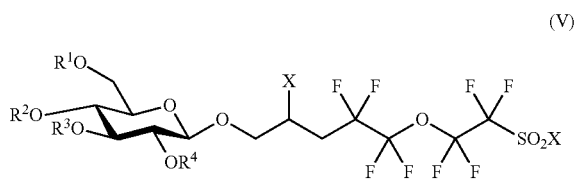

(V)

wherein each X is independently halo and each $R^{1-4}$ is independently H or a hydroxyl protecting group. For example, in some embodiments, each of $R^{1-4}$ is H. In other embodiments, one or more of $R^{1-4}$ can be acetyl. Of course, the stereochemistry of the saccharide moiety can have the stereochemistry of any of the naturally occurring sugars, including pyranose, furanose, or straight chain forms.

The following literature is incorporated herein by reference. For general reviews of PAGs, see Shirai and Tsunooka, "Photoacid and photobase generators: chemistry and applications to polymeric materials" *Progress in Polymer Science* 1996, 21(1), 1-45; and Shirai, et al., "Development of novel photosensitive polymer systems using photoacid and photobase generators" *Journal of Photopolymer Science and Technology* 2002, 15(5), 715-730.

For preparation of, and reactions involving, benzyl and nitrobenzyl organic chromophores, see Houlihan et al., "Design, synthesis, characterization, and use of all-organic, nonionic photogenerators of acid", *Chemistry of Materials* 1991, 3(3), 462-71; Hasan et al., "Photolabile Protecting Groups for Nucleosides: Synthesis and Photodeprotection Rates", *Tetrahedron*, Vol. 53, No. 12, pp. 4247-4264, 1997; and Serafinowski and Garland, *J Am. Chem. Soc.* 2003, 125, 962-965.

For preparation of, and reactions involving, imide and diimide organic chromophores, see Iwashima et al., "Synthesis of i- and g-line sensitive photoacid generators and their application to photopolymer systems", *Journal of Photopolymer Science and Technology* 2003, 16(1), 91-96;

Okamura et al., "I-line sensitive photoacid generators and their use for photocrosslinking of polysilane/diepoxyfluorene blend", *Journal of Photopolymer Science and Technology* (2003), 16(1), 87-90; Okamura et al., "Evaluation of quantum yields for decomposition of 1-line sensitive photoacid generators", *Journal of Photopolymer Science and Technology* (2003), 16(5), 701-706; Okamura et al., "I-line sensitive photoacid generators having thianthrene skeleton", *Journal of Photopolymer Science and Technology* (2004), 17(1), 131-134.

For compounds and preparations of various starting materials that can be linked to the saccharide compounds of the invention, see U.S. Pat. No. 6,316,639 (Fritz-Langhals; "Process for the preparation of cyclic N-hydroxy-dicarboximides"); U.S. Pat. No. 6,582,879 (Choi et al.; "Reactive photo acid-generating agent and heat-resistant photoresist composition with polyamide precursor"); U.S. Pat. No. 6,692,893 (Ohsawa et al.); U.S. Pat. No. 7,105,267 (Hatakeyama et al.); and U.S. Pat. No. 7,163,776 (Sasaki et al.); and U.S. Patent Application Publication No. 2005/0186505 (Kodama et al.), which describe useful organic chromophore moieties that can be used in conjunction with the saccharides and linkers of the invention.

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

The variable groups defined in the following Examples are for illustrative purposes. Certain groups, ranges, and specific variables that can be employed in the various embodiments are further described above in the summary and detailed description. General techniques for preparing photoacid generator compounds are known in the art. For example, see PCT Application Publication No. WO 2007/124092 (Ober et al.), incorporated herein by reference.

Example 1

Synthesis of Saccharide Photoacid Generators

Photoacid generator compounds containing saccharide substituted chains were prepared as follows.

Tetra-O-acetyl-β-D-glucopyranoside iodo-semifluoroalkyl fluoride

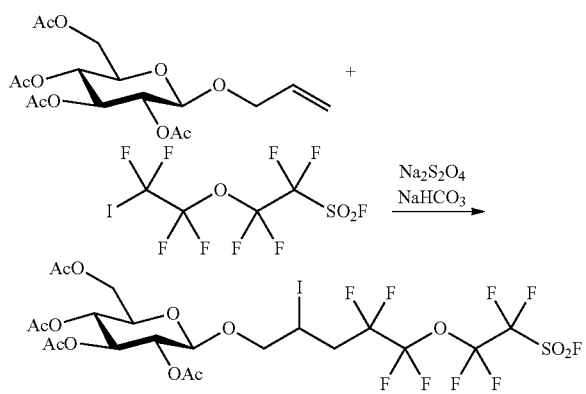

Allyl-tetra-O-acetyl-β-D-glucopyranoside (1.8 g, 4.6 mmol) and $ICF_2CF_2OCF_2CF_2SO_2F$ (4.8 g, 11.3 mmol) were dissolved in the mixture of 3 mL water and 6 mL acetonitrile. The mixture was then bubbled with nitrogen for 30 min. Then, $NaHCO_3$ (1.2 g, 14.3 mmol) and $Na_2S_2O_4$ (1.6 g, 9.2 mmol) were added. The mixture was stirred at room temperature overnight. After the reaction, the mixture was poured into 20 mL water. The aqueous solution was then extracted with ethyl ether. The ethyl ether solution was washed with brine and dried over anhydrous MgSO$_4$. After the evaporation, the crude product was obtained as sticky oil. Yield 3.2 g (85%). The crude product was used without purification for the next step reaction.

Tetra-O-acetyl-β-D-glucopyranoside semifluoroalkyl fluoride

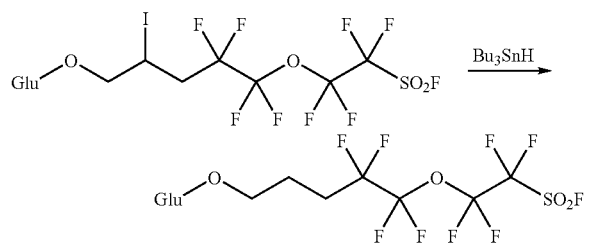

Iodo-semifluoroalkyl tetra-O-acetyl-β-D-glucopyranoside (3.2 g, 3.9 mmol) was dissolved in 10 mL ethyl ether. Tributyltin hydride (1.4 mL, 36.7 mmol) was slowly added under nitrogen. After the addition was over, the solution was reflux overnight. Then, iodine was added to quench the excessive tributyltin hydride, followed by adding 10 mL saturated aqueous solution of KF. The mixture was kept stirring for several hours. After the white precipitates were filtered, the ethyl ether solution was separated and dried over anhydrous MgSO$_4$. The yield of this reaction is 80% (2.2 g).

Tetra-O-acetyl-β-D-glucopyranoside semifluoroalkyl sulfonate

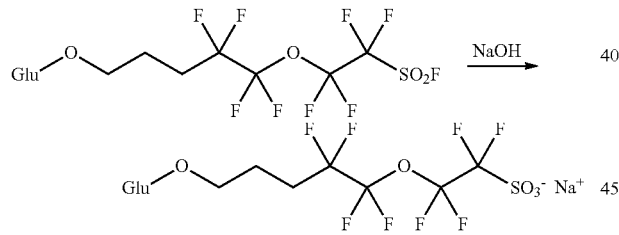

Tetra-O-Acetyl-β-D-glucopyranoside semifluoroalkyl fluoride (3.4 g, 5 mmol) and NaOH (0.4 g, 10 mmol) were added into 20 mL water. The mixture was refluxed at 90° C. overnight. After the water was evaporated, 10 mL anhydrous ethanol was added to precipitate NaF. The product was obtained by evaporating ethanol after NaF was filtered. 33 g crude product was obtained. Yield=93%.

Triphenylsulfonium tetra-O-acetyl-β-D-glucopyranoside semifluoroalkyl sulfonate

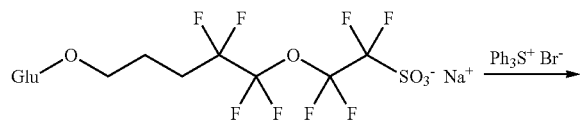

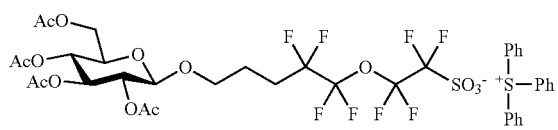

Tetra-O-acetyl-β-D-glucopyranoside semifluoroalkyl sulfonate (2.3 g, 3.25 mmol) and triphenylsulfonium bromide (1.1 g, 3.2 mmol) were mixed together in 20 mL water. The mixture was kept stirring overnight and extracted with chloroform. The chloroform solution was separated and dried over anhydrous MgSO$_4$. After the evaporation of chloroform, 0.3 g compound was obtained as yellowish crystal. Yield=97%.

Any available saccharide can be used to prepare similar PAGs. For example, in place of tetra-O-acetyl-β-D-glucopyranoside, tetra-O-acetyl-β-D-galactopyranoside can be used as the starting saccharide. Also, allyl tetra-O-acetyl-α-D-galactopyranoside has been prepared, which provides a PAG with an alternative stereochemical configuration at the sugar anomeric position. Other variations and combinations of these approaches will be readily recognized by those of skill in the art.

Example 2

Synthesis of Disaccharide Photoacid Generators

Using reaction conditions similar to those of Example 1, a disaccharide PAG was prepared from α-D-cellobiose octaacetate, which was purchases from Sigma-Aldrich.

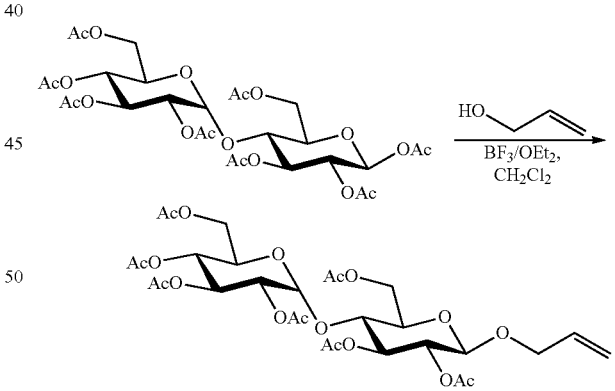

Allyl alcohol and α-D-cellobiose octaacetate were combined in the presence of boron trifluoride diethyl etherate to provide the allyl alcohol product in 89% yield. See *Bioorg. Med. Chem. Lett.* 16 (2006) 5827-5831. As in Example 1, the glycoside was combined with ICF$_2$CF$_2$OCF$_2$CF$_2$SO$_2$F in the presence of NaHCO$_3$ and Na$_2$S$_2$O$_4$, followed by reduction and sulfonyl fluoride hydrolysis to provide the sulfonic acid sodium salt. Hydrolysis of the acetyl groups and ion exchange with a triphenylsulfonium bromide provided the heptahydroxyl PAG below.

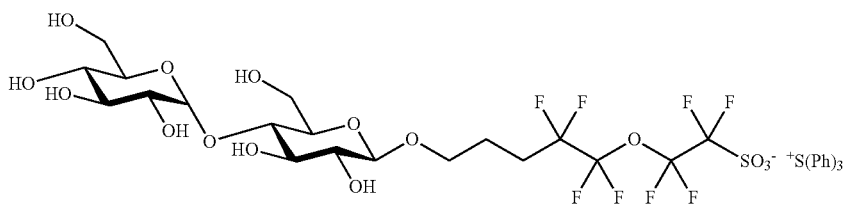

Of course, other cations can be prepared by using a diphenyliodonium halide in place of triphenylsulfonium bromide.

Example 3

Synthesis of Various Non-Ionic Photoacid Generators

Nonionic photoacid generators according to various embodiments can be prepared as described below. Compounds 3-1 can be prepared as described in Example 1, using $ICF_2CF_2OCF_2CF_2SO_2F$ as an initial starting material, or by conducting a halogen exchange reaction on the sulfonyl fluoride to provide the corresponding sulfonyl chloride.

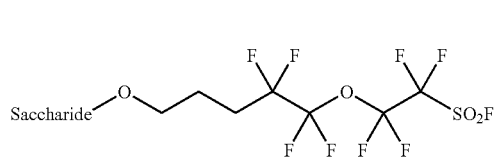

(3-1)

Compounds such as 3-1 can be used to prepare non-ionic PAGs as described below.

Imide-based PAGs can be prepared by reaction of the corresponding N-hydroxyimide with an appropriate sulfonyl fluoride, such as compound 3-1, in the presence of a base, as illustrated in Scheme 3-1. The imide can be optionally substituted with one to four $R^6$ groups by starting the preparation with the corresponding substituted imide.

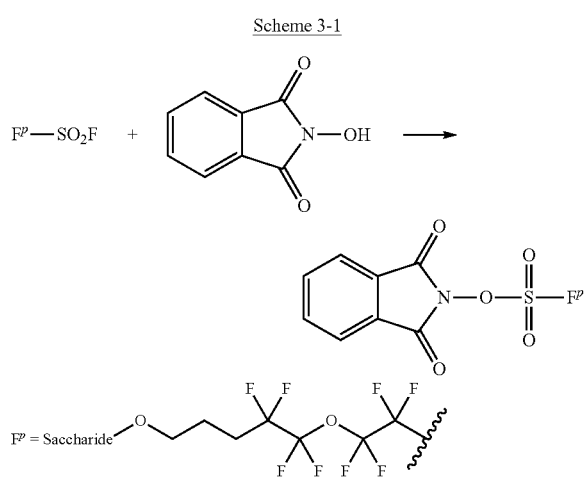

Scheme 3-1

Non-ionic diimide-based PAGs can be prepared by starting the preparation with the corresponding optionally substituted diimide.

A nitrobenzyl non-ionic PAG can be prepared either by reacting a silver sulfonate with nitrobenzyl bromide or by reacting a nitrobenzyl alcohol with a sulfonyl fluoride in the presence of coupling reagents, as illustrated in Scheme 3-2. One to four $R^6$ groups can optionally be included on the starting material by using the appropriate commercially available material and/or suitable standard synthetic manipulations.

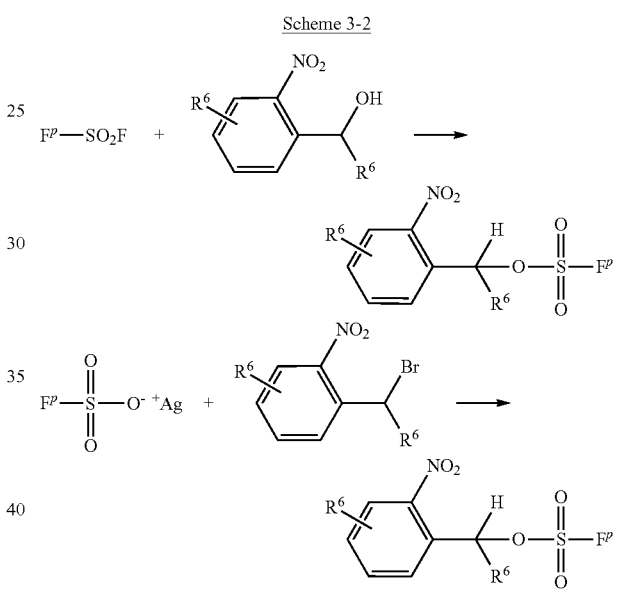

Scheme 3-2

In certain embodiments, $R^6$ can be H or $(C_1$-$C_6)$alkyl. In some embodiments, $R^6$ can be H, halo, alkyl, alkoxy, carboxy, cyano, acyl, acyloxy, trifluoromethyl, amino, or nitro.

Other nonionic PAGs of the invention are illustrated below.

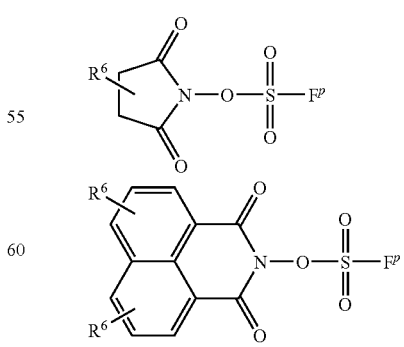

Any of the PAGs described herein can be linked together to form dimers, in various combinations, using the groups $R^6$ to form linking groups between the PAGs, for example, to prepare the compounds of Formula II.

Further examples of non-ionic PAGs include the following formulas:

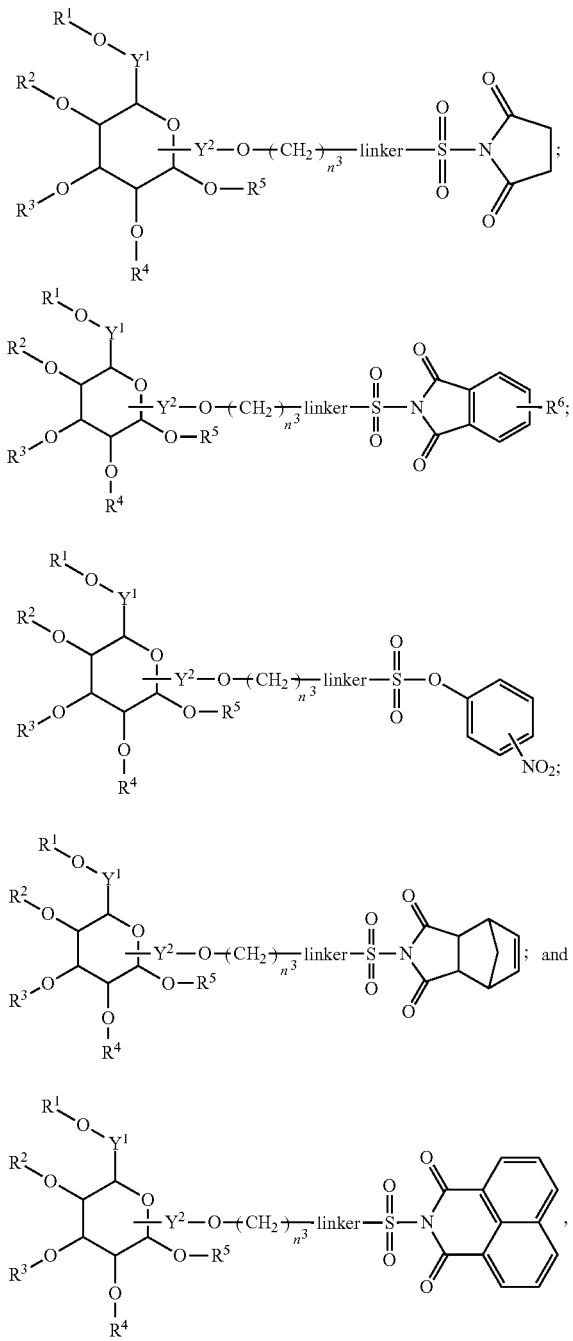

wherein each variable is defined above. Aryl, alkyl, heteroaryl, and heterocycle groups can be substituted with various substituents, such as one or more $R^6$ groups.

Example 4

Saccharide Group Substituents and Preparation

The saccharide groups of the PAG fluoroorganic moieties, for example, groups of Formula III, can be modified to provide varying characteristics to the PAGs. Hydroxyl moieties of the initial saccharides can be modified prior to, or after, preparation of the PAG. Often hydroxyl group manipulation is more conveniently carried out on the saccharide starting materials. An example of a standard hydroxyl group manipulation is illustrated in Scheme 4-1.

Scheme 4-1

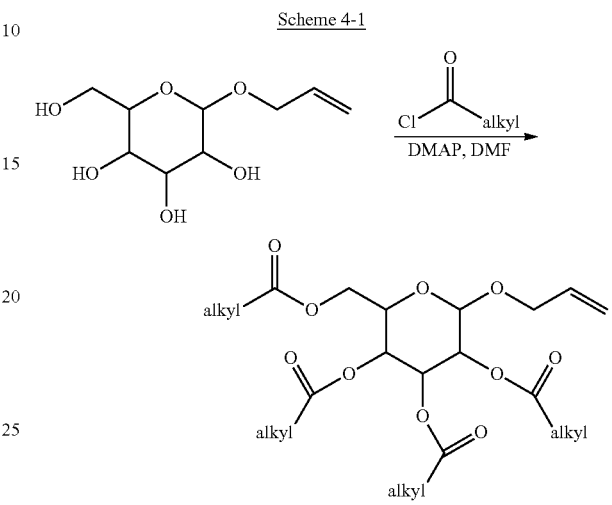

A variety of acid chlorides can be used to protect the hydroxyl groups of the saccharides. Several commercially available acid chlorides include linear, branched, and vinyl-containing acid chlorides. For example, suitable acid chlorides include compounds of the formula Cl—C(=O)—R where R is methyl, ethyl, propyl, pentyl, nonyl, undecyl, hexadecyl, t-butyl, 1,1-dimethylbutyl, 1,1-diethylbutyl, 2-methylpentyl, vinyl, 1-methylvinyl, 1-propenyl, and 3-butenyl. The alkyl group of Scheme 4-1 can also be replaced by a cycloalkyl or heteroaryl group, such as for the following commercially available acid chlorides:

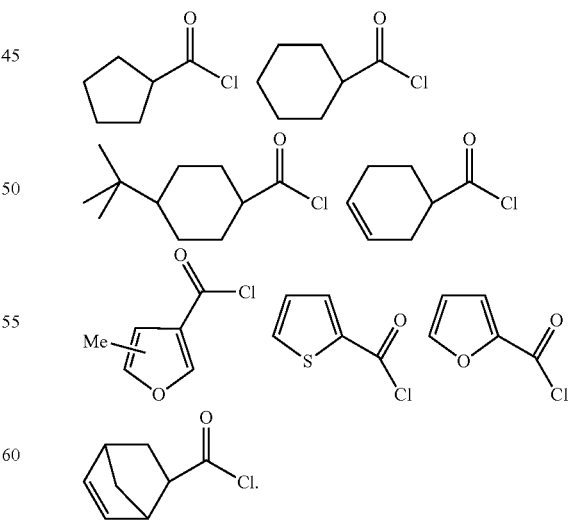

The acid chloride can also be an optionally substituted benzoyl chloride, such as the following commercially available acid chlorides:

33

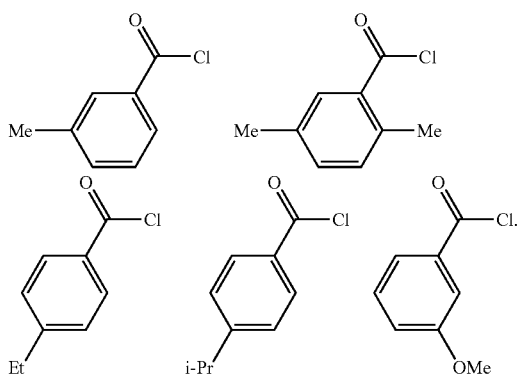

As an alternative to the use of acid chlorides, various alkyl halides can be used to facilitate substitutions on the saccharide hydroxyl groups. A general example is illustrated in Scheme 4-2.

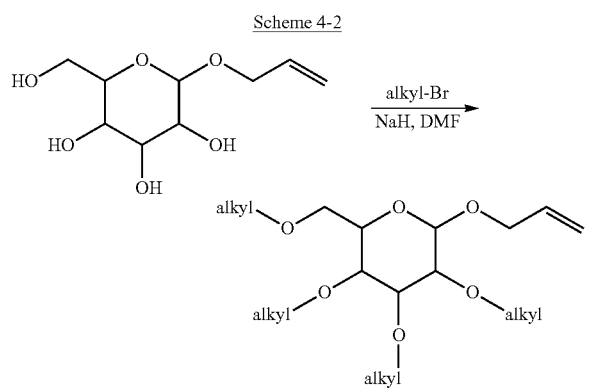

Syntheses of the following protected saccharides are known and can be used to prepare sweet PAGs.

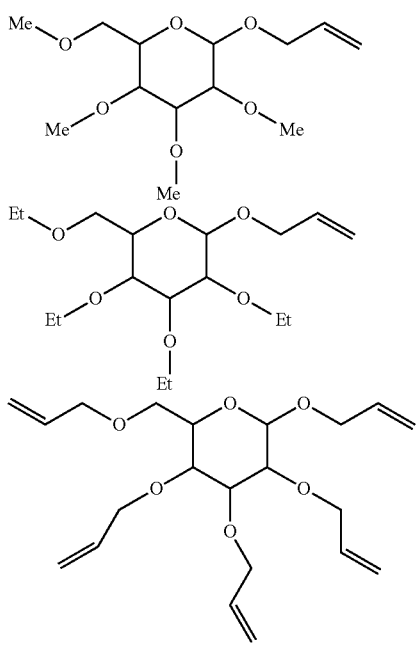

34

PAG with two or more fluoroorganic moieties can be prepared from the penta-allyl saccharide by the techniques described in Example 1.

Using similar methods, a tetra-Boc protected saccharide can be prepared using, for example, Boc-anhydride and DMAP in DMF.

Example 5

Preparation of Non-Ionic Photoacid Generators

Nonionic photoacid generators according to various embodiments can be prepared as described below. The synthesis of 4,6-O-acetyl-β-D-glucopyranoside semifluoroalkyl fluoride (5.1) was described in Example 1. The corresponding disaccharide PAGs can also be prepared by using the sulfonyl fluoride disaccharide intermediate described in Example 2. Alkyl fluoride 5.1 can be coupled to nitrobenzene derivative 5.2 in the presence of a base, such as a hindered amine base, and a suitable solvent, such as acetone, to provide nitrobenzene PAGs 5.3, wherein R is a substituent as described herein, for example, hydrogen, nitro, alkyl, halo, alkoxy, fluoroalkyl, cyano, etc. Specific examples of R include H, $NO_2$, $CH_3$, F, $OCH_3$, $CF_3$, and CN.

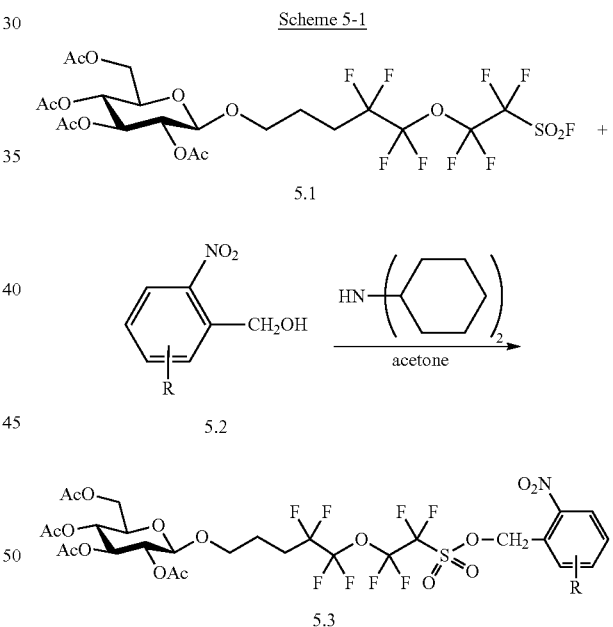

Nitrobenzenes 5.2 can have one to four R groups. Nitrobenzenes 5.2 may be commercially available from suppliers such as Aldrich Fine Chemicals (Milwaukee, Wis.), or they may be prepared from commercially available compounds using standard synthetic techniques. Additionally, the benzyl alcohol moiety of nitrobenzenes 5.2 can optionally be protected with a hydroxyl protecting group.

An example of the preparation of an imide-based PAG is illustrated in Scheme 5-2. Alkyl fluoride 5.1 can be coupled to imide 5.4 in a suitable solvent, such as acetone, and optionally in the presence of a base, such as dicyclohexyl amine, to provide saccharide imide PAG 5.4.

Scheme 5-2

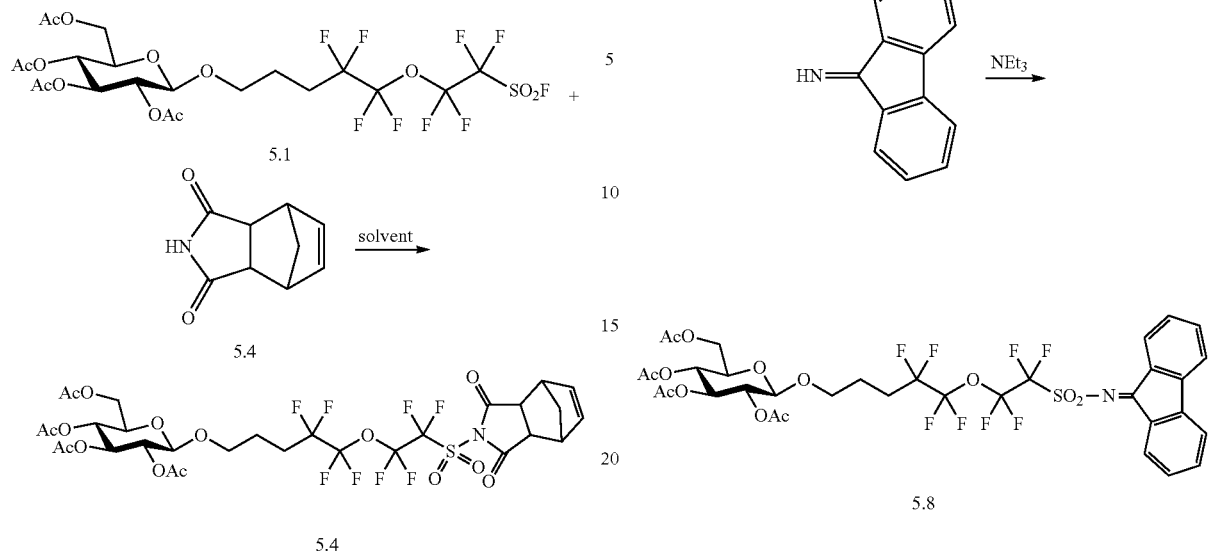

An example of the preparation of a diimide-based PAG is illustrated in Scheme 5-3. Two equivalents of alkyl fluoride 5.1 can be coupled to a diimide, such as pyrrolo[3,4-f]isoindole-1,3,5,7(2H,6H)-tetraone (5.5), or the corresponding naphthalene or anthracene diimide, in a suitable solvent and optionally in the presence of a base, such as triethylamine, to provide saccharide diimide PAG 5.6.

For each of the PAGs described in this example, alkyl fluoride 5.1 can be replaced with other saccharide containing groups, such as the disaccharide alkyl fluoride described in Example 2, or other disaccharide moieties described herein, as would be readily recognized by one skilled in the art.

Scheme 5-3

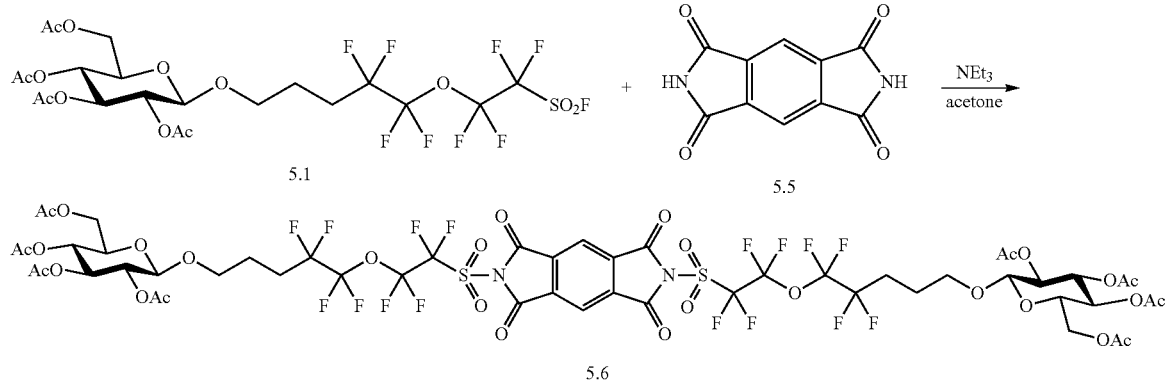

An example of the preparation of a fluorenimine-based PAG is illustrated in Scheme 5-4. Alkyl fluoride 5.1 can be coupled to a fluorenimine, such as 9H-fluoren-9-imine (5.7), or an optionally substituted derivative thereof, in a suitable solvent and optionally in the presence of a base, such as triethylamine, to provide the saccharide fluorenimine-based PAG 5.8.

Scheme 5-4

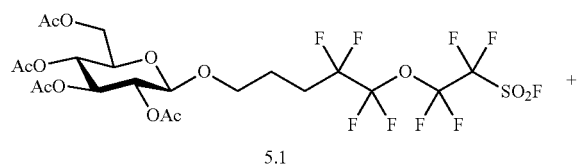

Example 6

Preparation of Ionic Photoacid Generators

Ionic photoacid generators according to various embodiments can be prepared as described below. The synthesis of 4,6-O-acetyl-β-D-glucopyranoside semifluoroalkyl fluoride (5.1) was described in Example 1. The corresponding disaccharide PAGs can also be prepared by using the sulfonyl fluoride disaccharide intermediate described in Example 2. An amine-linked dimer of alkyl fluoride 5.1 can be prepared by reacting two equivalents of sulfonyl fluoride 5.1 with ammonia in the presence of a hindered amine base, such as triethylamine, to provide disubstituted amine 6.1. Combining amine 6.1 with a base, such as lithium carbonate, can provide a deprotonated intermediate, which can be combined with a triphenylsulfonyl halide to provide ionic PAG 6.2.

Scheme 6-1

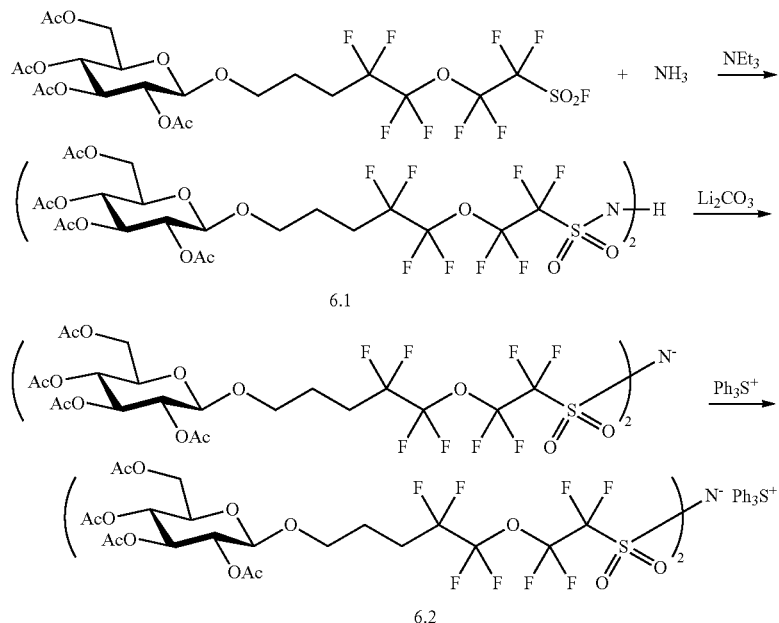

Derivatives of ionic PAG 6.2 can be prepared by using a substituted amine in place of ammonia (or an ammonia equivalent) in Scheme 6.1. For example, as illustrated in Scheme 6.2, alkyl fluoride 5.1 can be coupled to trifluoromethanesulfonamide to provide disulfonamide 6.3. Disulfonamide 6.3 can be deprotonated with a suitable base, followed by cation exchange with a triphenylsulfonyl halide to provide ionic PAG 6.4.

For each of the PAGs described in this example, alkyl fluoride 5.1 can be replaced with other saccharide containing groups, such as the disaccharide alkyl fluoride described in Example 2, or other disaccharide moieties described herein, as would be readily recognized by one skilled in the art.

All literature and patent citations above are hereby expressly incorporated by reference at the locations of their citation. Specifically cited sections or pages of the above cited Scheme 6-2

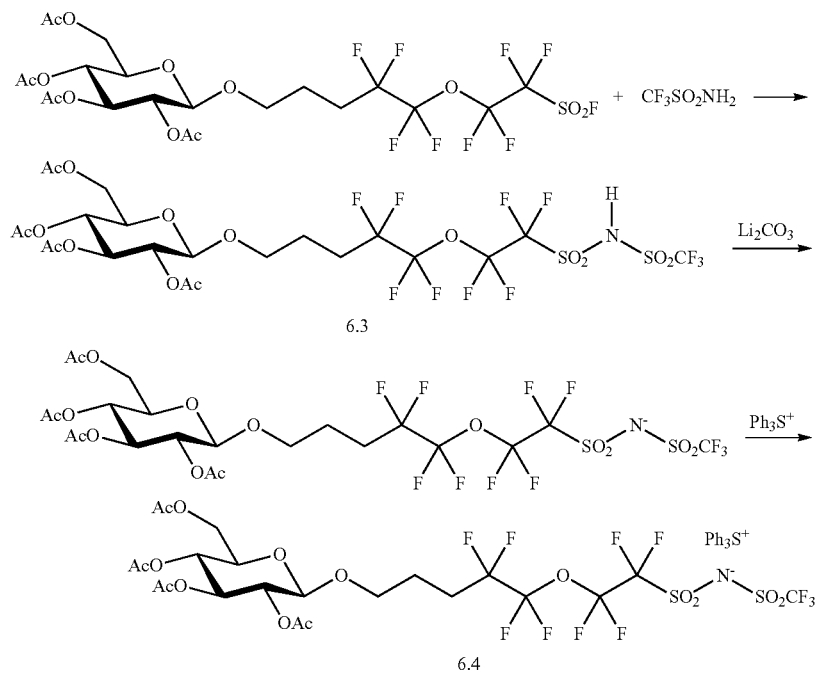

works are incorporated by reference with specificity. The invention has been described in detail sufficient to allow one of ordinary skill in the art to make and use the subject matter of the following Embodiments. It is apparent that certain modifications of the methods and compositions of the following Embodiments can be made within the scope and spirit of the invention.

What is claimed is:

1. An anion of Formula I:

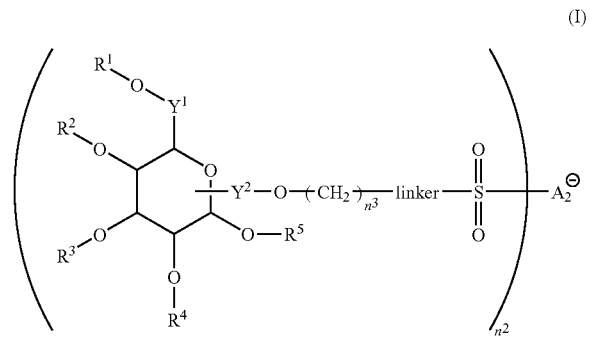

wherein
- $A_2$ is O or N;
- $n^2$ is 1 when $A_2$ is O and $n^2$ is 2 when $A_2$ is N;
- $n^3$ is 0 to about 10;
- $Y^1$ is $CH_2$ and $Y^2$ is direct bond, or $Y^1$ is direct bond and $Y^2$ is $CH_2$;
- one of $R^{1-5}$ is a direct bond to the group $Y^2$ and each of the remaining $R^{1-5}$ is independently H, hydroxyl protecting group, alkyl, cycloalkyl, heterocycle, aryl, heteroaryl, or saccharide;
- linker is a diradical carbon chain comprising one to about 20 carbon atoms wherein the chain is optionally interrupted by one to five oxygen atoms, and each carbon atom is substituted with zero, one, or two halo groups, or linker is a direct bond;
- any alkyl, cycloalkyl, heterocycle, aryl, heteroaryl, or saccharide is optionally substituted with one to five halo, ($C_1$-$C_6$)alkyl, alkoxy, acyl, alkoxyacyl, acyloxy, trifluoromethyl, trifluoromethoxy, hydroxy, cyano, carboxy, nitro, oxo, or —$N(R^x)_2$ groups, wherein each $R^x$ is independently H, alkyl, aryl, acyl, or aroyl.

2. The anion of claim 1 wherein $A_2$ is O and $n^2$ is 1.

3. The anion of claim 1 wherein at least one carbon of linker is substituted with two fluoro groups, or linker is a direct bond.

4. The anion of claim 1 wherein linker comprises —C($CF_3$)$_2$—, —($CF_2$)—O—($CF_2$)$_2$—O—($CF_2$)—, —($CF_2$)$_2$—O—($CF_2$)$_2$—, —($CF_2$)$_n$— wherein n is 1 to about 6, or a direct bond.

5. The anion of claim 1 wherein $n_3$ is 3.

6. The anion of claim 1 wherein $R^5$ is a direct bond to $Y^2$.

7. The anion of claim 1 wherein each of $R^{1-5}$ that are not directly bonded to the group $Y^2$ is H or a hydroxyl protecting group.

8. The anion of claim 1 wherein three of $R^{1-5}$ that are not directly bonded to the group $Y^2$ are H or a hydroxyl protecting group, and one is a saccharide.

9. The anion of claim 7 having the structure:

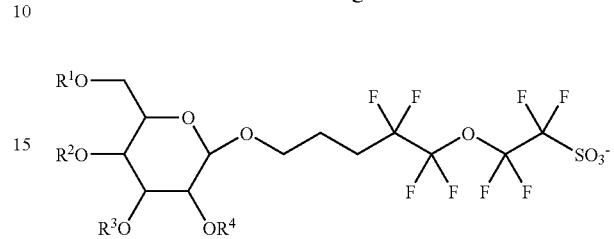

wherein each $R^{1-4}$ is independently H or a hydroxyl protecting group.

10. The anion of claim 8 having the structure:

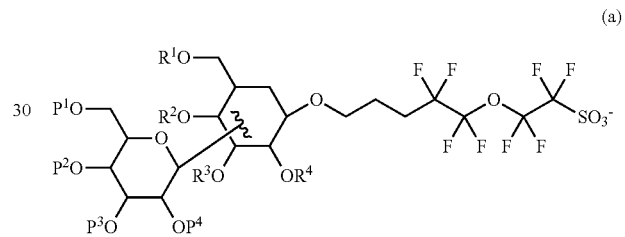

wherein one of the $R^{1-4}$ groups is a direct bond to the anomeric carbon of saccharide (a), the other $R^{1-4}$ groups are each independently H or hydroxyl protecting groups, and each of the $P^{1-4}$ groups is independently H or a hydroxyl protecting group.

11. The anion of claim 8 having the structure:

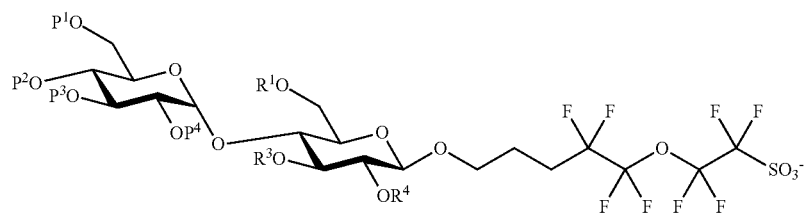

wherein each of $R^{1,3,4}$ is independently H or a hydroxyl protecting group, and each of $P^{1-4}$ is independently H or a hydroxyl protecting group.

12. A compound comprising the anion of claim 1 and a cation of Formula IV:

wherein $A_1$ is I or S; $n^1$ is 2 when $A_1$ is I, and $n^1$ is 3 when $A_1$ is S; and each $R^0$ is independently alkyl, cycloalkyl, heterocycle, aryl, or heteroaryl;

wherein the compound is a photoacid generator.

13. A compound of Formula II:

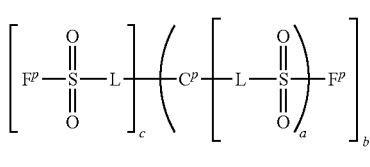

wherein
a is 1 or 2 wherein b is 1 and c is 0; or
b is 1 or 2 wherein a is 1 and c is 0; or
c is 2 and a and b are both 1;
L is O or a direct bond;
$C^p$ is an organic chromophore that includes at least one aryl, heteroaryl, heterocyclic, or carbocyclic rings containing 4 to 14 ring atoms, which optionally includes one to eight substituents, and which optionally includes a linker to an adjacent oxygen atom in Formula II, wherein the linker is an optionally substituted alkyl or =N—;
$F^p$ is a fluoroorganic group of Formula III:

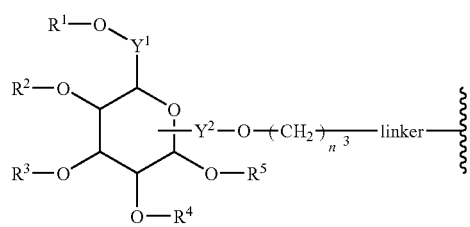

wherein $n^3$ is 0 to about 10;
$Y^1$ is $CH_2$ and $Y^2$ is direct bond, or $Y^1$ is direct bond and $Y^2$ is $CH_2$;
one of $R^{1-5}$ is a direct bond to the group $Y^2$ and each of the remaining $R^{1-5}$ is independently H, alkyl, cycloalkyl, heterocycle, aryl, heteroaryl, or saccharide;
linker is a diradical carbon chain comprising one to about 20 carbon atoms wherein the chain is optionally interrupted by one to five oxygen atoms, and each carbon atom is substituted with zero, one, or two halo groups, or linker is a direct bond;
any alkyl, cycloalkyl, heterocycle, aryl, heteroaryl, or saccharide is optionally substituted with one to five halo, $(C_1-C_6)$alkyl, alkoxy, acyl, alkoxyacyl, acyloxy, trifluoromethyl, trifluoromethoxy, hydroxy, cyano, carboxy, nitro, oxo, or —N(R$^x$)$_2$ groups, wherein each R$^x$ is independently H, alkyl, aryl, acyl, or aroyl.

14. The compound of claim 13 wherein Formula II has the structure of Formula IIA:

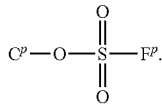

15. The compound of claim 13 wherein Formula II has the structure of Formula IIB:

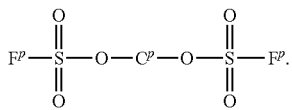

16. The compound of claim 13 wherein linker comprises —C(CF$_3$)$_2$—, —(CF$_2$)—O—(CF$_2$)$_2$—O—(CF$_2$)—, —(CF$_2$)$_2$—O—(CF$_2$)$_2$—, —(CF$_2$)$_n$— wherein n is 1 to about 6, or linker is a direct bond; and $n^3$ is about 3.

17. The compound of claim 13 wherein $C^p$ is:

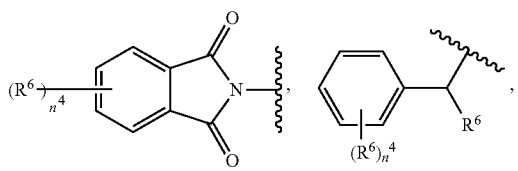

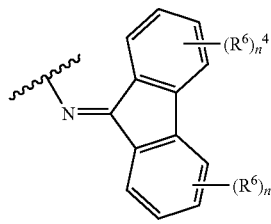

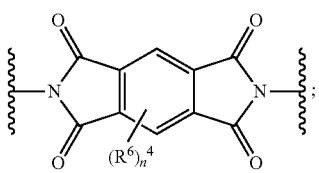

wherein $n^4$ is 1-5; and
each R$^6$ is independently H, alkyl, cycloalkyl, heterocycle, aryl, heteroaryl, halo, $(C_1-C_6)$alkyl, alkoxy, acyl, alkoxyacyl, acyloxy, trifluoromethyl, trifluoromethoxy, hydroxy, cyano, carboxy, nitro, oxo, or —N(R$^x$)$_2$ groups, wherein each R$^x$ is independently H, alkyl, aryl, acyl, or aroyl.

18. The compound of claim 13 wherein Formula III is:

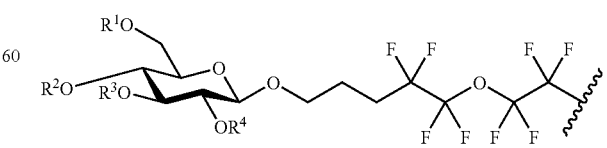

wherein each of $R^{1-4}$ is independently H or a hydroxyl protecting group.

19. The compound of claim 13 wherein Formula III is:

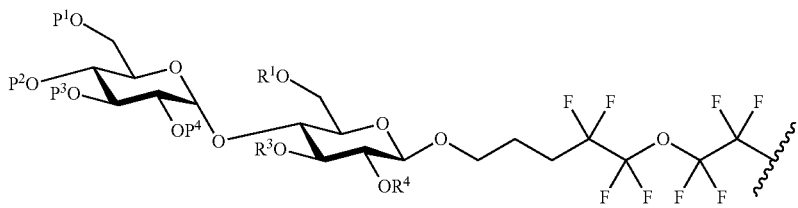

wherein each of $R^{1,3,4}$ is independently H or a hydroxyl protecting group, and each of $P^{1-4}$ is independently H or a hydroxyl protecting group.

20. A compound of Formula VI:

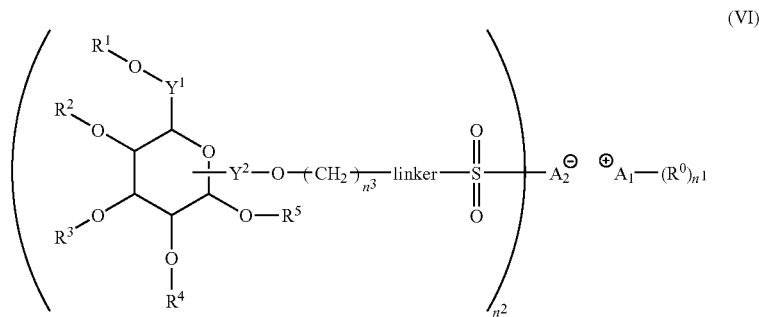

(VI)

wherein
- $A_1$ is I or S;
- $A_2$ is O or N;
- $n^1$ is 2 when $A_1$ is I, and $n^1$ is 3 when $A_1$ is S;
- $n^2$ is 1 when $A_2$ is O and $n^2$ is 2 when $A_2$ is N;
- $n^3$ is 0 to about 10;
- $Y^1$ is $CH_2$ and $Y^2$ is direct bond, or $Y^1$ is direct bond and $Y^2$ is $CH_2$;
- each $R^0$ is independently alkyl, cycloalkyl, heterocycle, aryl, or heteroaryl;
- one of $R^{1-5}$ is a direct bond to the group $Y^2$ and each of the remaining $R^{1-5}$ is independently H, alkyl, cycloalkyl, heterocycle, aryl, heteroaryl, or saccharide;
- linker is a diradical carbon chain comprising one to about 20 carbon atoms wherein the chain is optionally interrupted by one to five oxygen atoms, and each carbon atom is substituted with zero, one, or two halo groups, or linker is a direct bond;
- any alkyl, cycloalkyl, heterocycle, aryl, heteroaryl, or saccharide is optionally substituted with one to five halo, $(C_1-C_6)$alkyl, alkoxy, acyl, alkoxyacyl, acyloxy, trifluoromethyl, trifluoromethoxy, hydroxy, cyano, carboxy, nitro, oxo, or —$N(R^x)_2$ groups, wherein each $R^x$ is independently H, alkyl, aryl, acyl, or aroyl.

21. The compound of claim 20 wherein $R^0$ is aryl or heteroaryl.

22. The compound of claim 21 wherein the compound is a photoacid generator.

23. A chemical amplification type resist composition comprising the photoacid generator of claim 22, a resin, and a solvent system.

24. A composition comprising a compound of claim 22 and a resin that changes its solubility in an alkaline developer when contacted with an acid.

25. A composition comprising (a) a compound of claim 22, and (b) a compound that is capable of generating an acid upon exposure to radiation and that is not a compound of claim 22.

26. The composition of claim 25 further comprising a basic compound.

27. A method to form a pattern comprising:
a) applying onto a substrate a resist composition comprising a compound of claim 22, to provide a substrate with a coating;
b) heat treating the coating and exposing the coating to high energy radiation or electron beam through a photomask; and
c) optionally heat treating the exposed coating and developing the coating with a developer.

28. A compound of Formula V:

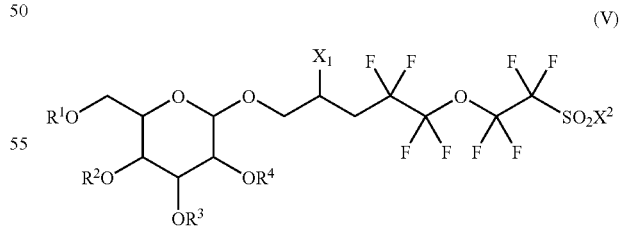

(V)

wherein $X^1$ is H or halo, $X^2$ is halo, and each of $R^{1-4}$ is independently H, a saccharide, or a hydroxyl protecting group.

* * * * *